(12) United States Patent
Zhang et al.

(10) Patent No.: US 9,034,340 B2
(45) Date of Patent: *May 19, 2015

(54) GENES ENCODING MAJOR CAPSID PROTEIN L1 OF HUMAN PAPILLOMA VIRUS

(71) Applicant: Shanghai Zerun Biotechnology Co., Ltd., Shanghai (CN)

(72) Inventors: Goaxia Zhang, Shanghai (CN); Qiong Shen, Shanghai (CN); Jianqiang Lei, Shanghai (CN); Jingyu Yuan, Shanghai (CN); Menghua Zhang, Shanghai (CN); Qianli Zhang, Shanghai (CN); Yinghua Xiong, Shanghai (CN); Roger Wei, Shanghai (CN); Ke Wu, Shanghai (CN)

(73) Assignee: Shanghai Zerun Biotechnology Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/296,700

(22) Filed: Jun. 5, 2014

(65) Prior Publication Data

US 2014/0328935 A1 Nov. 6, 2014

Related U.S. Application Data

(63) Continuation of application No. 12/744,190, filed as application No. PCT/CN2008/073167 on Nov. 24, 2008, now Pat. No. 8,795,676.

(30) Foreign Application Priority Data

| Nov. 23, 2007 | (CN) | 2007 1 0170934 |
| Nov. 23, 2007 | (CN) | 2007 1 0170935 |
| Nov. 23, 2007 | (CN) | 2007 1 0170936 |
| Jan. 15, 2008 | (CN) | 2008 1 0032654 |
| Jan. 15, 2008 | (CN) | 2008 1 0032655 |

(51) Int. Cl.
| *A61K 39/12* | (2006.01) |
| *C07K 14/005* | (2006.01) |
| *C12N 7/00* | (2006.01) |
| *C12N 15/81* | (2006.01) |

(52) U.S. Cl.
CPC ......... *C07K 14/005* (2013.01); *Y10T 428/2982* (2015.01); *A61K 39/12* (2013.01); *C12N 7/00* (2013.01); *C12N 15/81* (2013.01); *C12N 2710/18022* (2013.01); *C12N 2710/20022* (2013.01); *C12N 2710/20023* (2013.01); *C12N 2710/20034* (2013.01)

(58) Field of Classification Search
CPC ........ A61K 39/12; C07K 14/005; C12N 7/00; C12N 2710/20034; C12N 2710/18022; C12N 2710/20022; C12N 2710/20023; C12N 15/81
See application file for complete search history.

(56) References Cited

U.S. PATENT DOCUMENTS 6,436,402 B1 8/2002 Zhao et al.

FOREIGN PATENT DOCUMENTS

| WO | 2004084831 A2 | 10/2004 |
| WO | 2005032586 A1 | 4/2005 |
| WO | 2005047315 A2 | 5/2005 |
| WO | 2005097821 A1 | 10/2005 |

OTHER PUBLICATIONS

Advisory Action dated Jul. 9, 2012 in U.S. Appl. No. 12/744,190.
Genbank AAC09292 (1998).
Genbank AAP20601 (2005).
Genbank AAQ92369 (2003).
Li, P. et al., Chinese Journal of Experimental and Clinical Virology (2003) 12:310-314 (abstract only).
Office Action dated Apr. 25, 2012 in U.S. Appl. No. 12/744,190.
Office Action dated Sep. 29, 2011 in U.S. Appl. No. 12/744,190.
Schiller, J.T. et al., "Prospects for Cervical Cancer Prevention by Human Papilloma Virus Vaccination," Cancer Res. (2006) 66(21):10229-10232.
Sinclair, G. et al., "Synonymous codon usage bias and the expression of human glucocerebrosidase in the methylotrophic yeast, *Pichia pastoris*," Protein Expression and Purification (2002) 26:96-105.
Supplementary European Search Report in European Patent Application No. 08860834 dated Nov. 11, 2011.
Xie, F. et al., "Expression and identification of human papilloma virus type 18 L1 protein in *Pichia pastoris*," Chemical Abstracts, Mar. 20, 2008, 1 pg.

*Primary Examiner* — Benjamin P Blumel
*Assistant Examiner* — Rachel Gill
(74) *Attorney, Agent, or Firm* — Wood, Herron & Evans, L.L.P.

(57) ABSTRACT

The present invention discloses a codon-optimized gene encoding major capsid protein L1 of human papilloma virus, which is capable, after transduced into a yeast cell, of efficiently expressing the major capsid protein L1 of human papilloma virus. The present invention also discloses an immunogenic macromolecule which is essentially produced by expression of said codon-optimized gene encoding the major capsid protein L1 of human papilloma virus in a yeast cell. The present invention further discloses the use of said immunogenic macromolecule and a composition comprising said immunogenic macromolecule.

15 Claims, 3 Drawing Sheets

GENES ENCODING MAJOR CAPSID PROTEIN L1 OF HUMAN PAPILLOMA VIRUS

CROSS-REFERENCE TO RELATED APPLICATIONS

This application is a continuation of U.S. patent application Ser. No. 12/744,190, entitled "Genes Encoding Major Capsid Protein L1 of Human Papilloma Virus," filed on Aug. 13, 2010, which is a U.S. national phase filing under 35 U.S.C. §371 of International Patent Application No. PCT/CN2008/073167, filed on Nov. 24, 2008, which claims priority to and the benefit of the filing dates of Chinese Patent Application No. 200710170935.4, filed on Nov. 23, 2007, Chinese Patent Application No. 20071017936.9, filed on Nov. 23, 2007, Chinese Patent Application No. 200710170934.X, filed on Nov. 23, 2007, Chinese Patent Application No. 200810032654.7, filed on Jan. 15, 2008, and Chinese Patent Application No. 200810032655.1, filed on Jan. 15, 2008, the disclosures of which are incorporated by reference herein in their entireties.

FIELD OF THE INVENTION

The present invention relates to the field of biotechnology, particularly to the major capsid protein of human papilloma virus, gene coding the same, and preparation method and use of the same.

BACKGROUND OF THE INVENTION

Human papilloma virus (HPV) is a non-enveloped small double-stranded circular DNA virus belonging to polyomavirus subfamily of papova virus family. HPV can be spread through intimate contact among human beings, leading to such lesions in the infected persons as verruca vulgaris on the skin and condylomata acuminata around the anus and genitalia, which are ranked as sexually transmitted diseases. The results of investigation published by the International Agency for Research on Cancer in 1995 showed that HPV is closely responsible for cervical cancer. It is thus clear that HPV has become a pathogen that is severely harmful to human health. Therefore, it is much significant to develop highly efficient and inexpensive HPV vaccines for the prevention of cervical cancer in women and the sexually transmitted diseases caused by HPV infection.

More than 100 subtypes of HPV have been identified currently. Nearly 100% of the cervical cancer patients can be detected positive for the presence of high-risk HPV DNA in the pathologic tissues by using sensitive detection methods. In terms of the relationship between HPV subtypes and malignancies in genital tract of female patient, HPV can be classified into low-risk type and high-risk type. HPV6, 11, 34, 40 and 42 and the like are low-risk HPV subtypes, typically found in benign cervical lesions such as cervical condylomas and mild atypical hyperplasia of cervical epithelium; while HPV 16, 18, 31, 33, 35, 39, 45 are high-risk HPV subtypes, mostly found in severe atypical hyperplasia of cervical epithelium as well as cervical cancer. A series of studies on different human populations have substantiated that HPV 16 and 18 infections in genital tract are more highly associated with the occurrence of cervical cancer than other risk factors. Among cervical cancer patients, about 50 to 60% of the cases are caused by HPV 16 infection, about 14% by HPV 18, about 8% by HPV 45, and about 5% by HPV 31, with the remaining 23% of the cases caused by other HPV subtypes.

HPV is non-enveloped and globular in shape with a diameter of about 45 to 55 nm, having an icosahedrally symmetric deflective capsid consisting of 72 capsid particles. The virion capsid is essentially comprised of major capsid proteins (L1) and minor capsid proteins (L2). After being expressed in cells, major capsid proteins L1 can be self-assembled into capsid particles called virus-like particles (VLPs).

A normal woman has a life-time accumulative probability of about 40% for cervical infection by at least one subtype of HPV during her whole life. Therefore, it is of great importance to develop suitably-priced and advantageously protective vaccines against cervical cancer, especially vaccines against HPV 16 and HPV 18, for lowering the morbidity and mortality of cervical cancer in women.

Although some vaccines have been developed against HPV in the prior art, these vaccines generally have the problems of low expression efficiency of HPV protein, low activity of the expressed protein, inability of the protein to assemble into virus-like particles or undesirability of the immunological effect of the assembled particles. Consequently, there exists a need in the art for improved HPV vaccine products.

SUMMARY OF THE INVENTION

Objects of the present invention include providing a gene for the major capsid protein L1 of human papilloma virus, and preparation method and use of the same.

In a first aspect of the present invention, there is provided an isolated gene encoding the major capsid protein L1 of human papilloma virus, said gene having the codons preferred by *Pichia* yeast.

In another preferred embodiment, said gene encodes the major capsid protein L1 of human papilloma virus having an amino acid sequence set forth in SEQ ID NO: 10 or in positions 62 to 568 of SEQ ID NO: 10 (i.e., the major capsid protein L1 of human papilloma virus subtype 18). More preferably, said gene has a nucleotide sequence selected from those set forth in SEQ ID NO: 1, SEQ ID NO: 2 and SEQ ID NO: 3; or has a nucleotide sequence selected from those set forth in SEQ ID NO: 4, SEQ ID NO: 5 and SEQ ID NO: 6.

In another preferred embodiment, said gene encodes the major capsid protein L1 of human papilloma virus having an amino acid sequence set forth in SEQ ID NO: 11 (i.e., the major capsid protein L1 of human papilloma virus subtype 16). More preferably, said gene has a nucleotide sequence selected from those set forth in SEQ ID NO: 7, SEQ ID NO: 8 and SEQ ID NO: 9.

In a second aspect of the present invention, there is provided an expression vector comprising the sequence of said gene.

In another preferred embodiment, said expression vector is a *Pichia* yeast expression vector.

In a third aspect of the present invention, there is provided a genetically engineered host cell, said cell comprising said expressing vector or having said gene integrated into its genome.

In another preferred embodiment, said cell is *Pichia* yeast cell. More preferably, said *Pichia* yeast is selected from *Pichia* yeast X-33, GS115, KM71 and SMD1168 strains. Most preferably, said *Pichia* yeast is *Pichia* yeast X-33 strain.

In a fourth aspect of the present invention, there is provided an immunogenic macromolecule (i.e., virus-like particle). Said macromolecule, 50-80 nm in diameter, is self-assembled from the major capsid protein L1 of human papilloma virus, which is expressed by *Pichia* yeast.

In another preferred embodiment, said immunogenic macromolecule is prepared by the following method:

(1) culturing said host cell to allow said major capsid protein L1 of human papilloma virus to be expressed and to be self-assembled into said immunogenic macromolecule in said host cell;

(2) separating said immunogenic macromolecule.

In a fifth aspect of the present invention, there is provided a method for preparing said immunogenic macromolecule, said method comprising:

(1) culturing said host cell to allow said major capsid protein L1 of human papilloma virus to be expressed and to be self-assembled into said immunogenic macromolecule in said host cell;

(2) separating said immunogenic macromolecule.

In another preferred embodiment, step (2) as described above includes:

(a) disrupting the host cells obtained from step (1) to obtain a supernatant containing said immunogenic macromolecule; and (b) successively purifying the supernatant obtained from step (a) using POROS 50 HS column chromatography and CHT column chromatography to obtain said immunogenic macromolecule.

In another preferred embodiment, in step (b) as described above, purification using POROS 50 HS column chromatography is performed as follows: The supernatant obtain from step (a) is loaded onto a POROS 50HS column having been cleaned and equilibrated to allow said immunogenic macromolecule to bind to the column. After being rinsed and equilibrated, the column is eluted with a linear gradient of 100% buffer A to 100% buffer B, and the chromatographic peaks at 70-100 ms/cm are collected, wherein said buffer A contains 50±20 mM MOPS, 0.75±0.3 M NaCl and 0.05±0.02% Tween-80 (pH 6.5±1), and said buffer B contains 50±20 mM MOPS, 1.5M NaCl and 0.05±0.02% Tween-80 (pH 6.5±1); or Purification using CHT column chromatography is performed as follows: the product purified from POROS 50 HS column chromatography is loaded onto a CHT column having been cleaned and equilibrated. After being rinsed and equilibrated, the column is eluted with a linear gradient of buffer C to 100% buffer D, and the chromatographic peaks 50-70 ms/cm are collected, wherein said buffer C contains 50±20 mM MOPS, 0.5±0.2 M NaCl, 0.04±0.02 M PB and 0.05±0.02% Tween-80 (pH 6.5±1), and said buffer D contains 0.5±0.2M NaCl, 200 mM PB, and 0.05±0.02% Tween-80 (pH 6.5±1).

In a sixth aspect of the present invention, there is provided an immunogenic composition, said composition comprising:

(i) an effective amount of said immunogenic macromolecule; and (ii) a pharmaceutically acceptable carrier.

In another preferred embodiment, said pharmaceutically acceptable carrier comprises at least one of immunostimulant or adjuvant.

In another preferred embodiment, said adjuvant is an aluminium adjuvant.

In another preferred embodiment, said composition is a vaccine.

In a seventh aspect of the present invention, there is provided the use of said immunogenic macromolecule in the prevention or treatment of diseases related to human papilloma virus infection.

In an eighth aspect of the present invention, there is provided a method for preventing or treating diseases related to human papilloma virus infection, said method comprising administering to a subject in need of prevention or treatment an effective amount of said immunogenic macromolecule or said immunogenic composition.

In another preferred embodiment, said diseases related to human papilloma virus infection are selected from malignancies (such as cervical cancer, vaginal cancer, anal or perianal cancer, oropharyngeal cancer, maxillary sinus cancer, lung cancer) or cervical intraepithelial neoplasia.

Other aspects of the present invention will be apparent to one skilled in the art in view of the present disclosure.

DETAILED DESCRIPTION OF THE INVENTION

Figure 1:
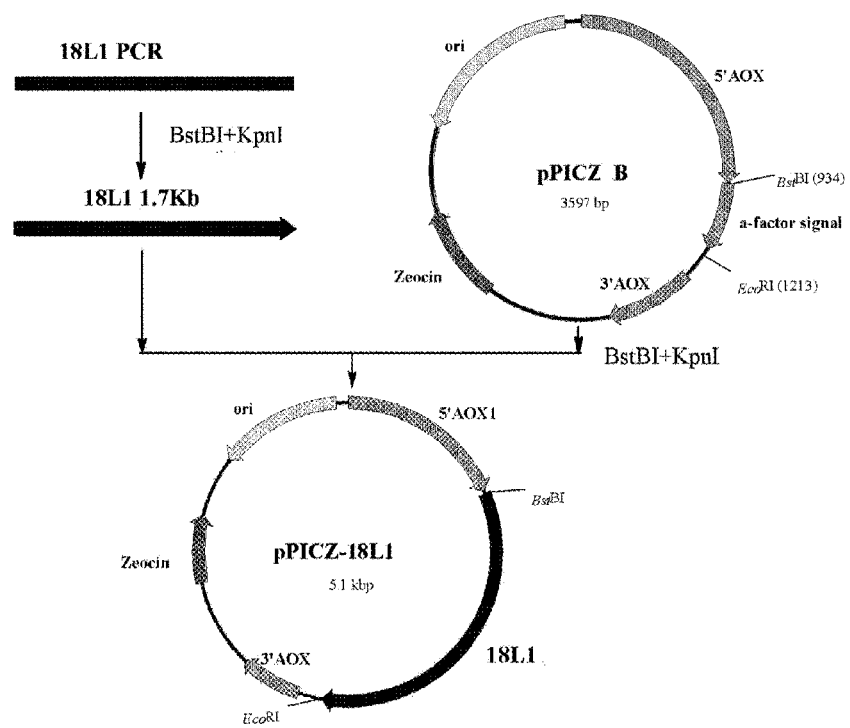
FIG. 1 is a schematic depiction of the construction of pPICZ-18L1 vector.

Through intensive research, the present inventors have for the first time disclosed a codon-optimized gene encoding the major capsid protein L1 of human papilloma virus, which is capable, when introduced into a yeast cell, of efficiently expressing the major capsid protein L1 of human papilloma virus which then self-assembles into virus-like particles, in an expression amount that meets the requirements of industrial production. The present invention also for the first time discloses an immunogenic macromolecule which is essentially produced by expression of said codon-optimized gene encoding the major capsid protein L1 of human papilloma virus in a yeast cell.

As used herein, said major capsid protein L1 of human papilloma virus is referred to, for short, as HPV L1 protein; said major capsid protein L1 of human papilloma virus subtype 18 is referred to, for short, as HPV18 L1 protein; and said major capsid protein L1 of human papilloma virus subtype 16 is referred to, for short, as HPV16 L1 protein. HPV L1 protein includes HPV18 L1 protein and HPV16 L1 protein, or truncated forms thereof.

As used herein, the term "immunogenic macromolecule" refers to a polymer macromolecule comprising a number of monomeric major capsid proteins L1 of human papilloma virus, preferably polymerized or assembled from a number of major capsid proteins L1 of human papilloma virus; said major capsid proteins L1 of human papilloma virus are encoded by a codon-optimized gene encoding the major capsid protein L1 of human papilloma virus and are expressed in yeast cell (preferably *Pichia* yeast cell). Said immunogenic macromolecule is granular in shape.

As used herein, "operably linked together" or "operably linked to" refers to a status in which certain portions of a linear DNA sequence can influence the activities of other portions of the same linear DNA sequence. For example, if a promoter controls the transcription of an encoding sequence, then it is operably linked to the encoding sequence.

As used herein, the phrase "comprising", "having" or "including" (or grammatical variants thereof) encompasses "containing", "substantially consisting of . . . ", "essentially consisting of . . . " and "consisting of . . . ". Concepts "substantially consisting of . . . ", "essentially consisting of . . . " and "consisting of . . . " are subordinate concepts of "comprising", "having" or "including".

Gene Encoding the Major Capsid Protein L1 of Human Papilloma Virus

Based on the object of expressing HPV L1 protein using yeast cell, the present inventors have, after repeated investigation, found an optimized gene encoding HPV L1 protein which is suitable to be efficiently expressed in yeast cell, particularly in *Pichia* yeast cell. Said optimized gene encodes a full-length or truncated HPV18 L1 protein. Alternatively, said optimized gene encodes a full-length HPV16 L1 protein.

It is well known to those skilled in the art that, although there exist 64 genetic codons, most organisms tend to utilize some of these codons. For example, the genes of yeast cell have a different preference for codons than do human genes. Due to degeneracy of genetic codons, each amino acid may be encoded by more than one codon, with the codons for the same amino acid having different frequencies of usage in wild-type genes. Yeast cell's preference for codons may result in low translation efficiency and expression levels of recombinant proteins.

Codon optimization according to the present invention is essentially achieved as follows. Firstly, modifications are made on the naturally-occurring gene encoding HPV L1 by optimizing the codons for all the corresponding amino acids of the gene and repeatedly conducting gene expression experiments on the optimized gene sequences so as to find a novel set of HPV DNA sequences suitable for expression in yeast cell. The gene encoding full-length HPV 18 L1 is set forth in Genbank accession no. AAP20601; the gene encoding truncated HPV 18 L1 is set forth in Genbank accession no. AAQ92369; and the gene encoding full-length HPV 16 L1 is set forth in Genbank accession no. AAC09292.

Furthermore, in order to avoid the presence of a high GC ratio in the transcribed mRNAs, the influence of mRNA secondary structure on the efficiency of translation, and the occurrence of common restriction sites, the present inventors have made alterations to some of the preferable codons, such as, the codon for asparagine (Asn) being altered from AAC to AAT; the codon for lysine (Lys) being altered from AAG to AAA; the codon for aspartic acid (Asp) being altered from GAT to GAC, the codon for phenylalanine (Phe) being altered from TTT to TTC; the codon for tyrosine (Tyr) being altered from TAC to TAT; and the codon for glycine (Gly) being altered from GGT to GGA, thus obtaining a altered, novel HPV DNA sequences.

In a preferred embodiment of the present invention, said gene encodes the major capsid proteins L1 of human papilloma virus having an amino acid sequence set forth in SEQ ID NO: 10 or in positions 62 to 568 of SEQ ID NO: 10 (i.e., HPV 18 L1). More preferably, said gene has a nucleotide sequence selected from those set forth in SEQ ID NO: 1, SEQ ID NO: 2 and SEQ ID NO: 3; or has a nucleotide sequence selected from those set forth in SEQ ID NO: 4, SEQ ID NO: 5 and SEQ ID NO: 6. Even more preferably, said gene has a nucleotide sequence set forth in SEQ ID NO: 1 or SEQ ID NO: 4. Most preferably, said gene has the nucleotide sequence set forth in SEQ ID NO: 1, which is a gene for truncated HPV 18 L1 corresponding to a truncated HPV 18 L1 protein with deletions of 61 amino acids at the N-terminus. Such a truncated gene is more favorably expressed in a recombinant vector without changing the activity of the protein.

In another preferred embodiment of the present invention, said gene encodes the major capsid proteins L1 of human papilloma virus having an amino acid sequence set forth in SEQ ID NO: 11 (i.e., HPV16 L1). More preferably, said gene has a nucleotide sequence selected from those set forth in SEQ ID NO: 7, SEQ ID NO: 8 and SEQ ID NO: 9. Most preferably, said gene has the nucleotide sequence set forth in SEQ ID NO: 7.

The codon-optimized gene provided by the present invention has the following advantages: 1) this optimized gene is more suitable for efficiently expressing target protein in yeast host and meets the requirements of industrial production; and 2) low cost, high yield and more uniform and stable quality of products can be achieved with the use of *Pichia* yeast expression system.

The present invention also provides a vector comprising said gene encoding HPV L1. Said vector may further comprise regulatory sequence(s) for expression which are operably linked to the sequence of said coding gene so as to facilitate the expression of said HPV L 1 protein. Any suitable vector can be used, especially those used for cloning and expression in yeast cell. More preferably, said expression vector is selected from currently commonly used yeast expression vectors, such as pPICZ, pPIC6, pGAPZ and pAO815. Such expression vectors are commercially available.

Moreover, recombinant cell comprising said gene encoding HPV L1 is also included in the present invention. Said recombinant cell is a yeast cell, particularly a *Pichia* yeast cell. More preferably, said *Pichia* yeast cell is selected from *Pichia* yeast X-33, GS115, KM71 and SMD1168 strains. These yeast cell strains are commercially available. Methods for introducing an exogenous gene into yeast cell are known in the art, for example, electrotransformation or protoplast transformation.

Method for producing HPV L1 is also included in the present invention. Said method comprises culturing said recombinant cell comprising said coding gene. Said method may include allowing the cells to express the encoded HPV L1 protein, and may further include separating and/or purifying the expressed protein. The HPV L1 protein obtained as above can be purified into essential homogeneity, for example, exhibiting a single band on SDS-PAGE electrophoresis.

The HPV L1 protein expressed in yeast cell according to the present invention can be used for preparing immunogenic macromolecule which can induce immune responses in vivo, particularly humoral immune responses.

As an embodiment of the present invention, the present inventors have designed, through optimization, several gene sequences suitable for expressing HPV L1 protein in *Pichia* yeast, which were then used for the total synthesis of full-length HPV L1 gene or its truncated form. The gene or its truncated form was cloned into existing *Pichia* yeast expression vector which was then used to construct recombinant *Pichia* yeast expression strain through homologous recombination and screening with high concentration antibiotics. The recombinant *Pichia* yeast was fermentatively cultured and then induced with methanol to highly express HPV L1 protein intracellularly, which is capable of concurrently self-assembling into virus-like particles (VLPs) intracellularly. The virus-like particles purified by chromatography of the supernatant obtained from disrupted cells had a purity of greater than 90% and were highly immunogenic when adsorbed to an aluminium adjuvant, permitting them to be used as a human vaccine against cervical cancer.

Protein Expression and Purification

HPV L1 protein can be efficiently expressed by culturing said recombinant cell comprising said gene encoding HPV L1, the expressed proteins being concurrently allowed to be self-assembled into immunogenic macromolecules. A method of expression and purification includes: (1) culturing said recombinant cell to allow said major capsid protein L1 of human papilloma virus to be expressed and to be concurrently self-assembled into immunogenic molecules in the recombinant cells; (2) disrupting the cells obtained from step (1) to obtain supernatant containing the immunogenic molecules; and (3) successively purifying the supernatant obtained from step (2) using POROS 50 HS column chromatography and CHT column chromatography to obtain said immunogenic macromolecules.

Preferably, cell culturing and protein expression are conducted as follows. The genetically engineered yeast according to the present invention is inoculated into activation media (YPD or LB or SOC) and cultured at 25 to 37° C. overnight. Then the activated fluid is inoculated into seed culture media (YPD or LB or SOC) and cultured at 25 to 37° C. overnight. Fermentation is conducted using basal salt medium (BSM1 or BSM2 or BSM3) added with trace amounts of salts (PTM1, PTM2, PTM3) at a temperature of 20 to 37° C. and an initial pH of 3 to 8. After the initial proliferation stage for about 15 to 30 hours, the dissolved oxygen value is maintained at 20 to 80% by adjusting the speed of stirring, air flow, and tank pressure. When the carbon source is completely consumed, the wet weight of yeast would reach about 50 to 150 g/L. At this time, glycerol or glucose solution is supplemented and the dissolved oxygen value is maintained at 20 to 80%. After a period of time of supplementation, the wet weight of yeast would reach about 50 to 500 g/L, at which time supplementation is stopped and methanol is added for induction while the pH value is maintained at pH 3 to 8. The dissolved oxygen value is maintained at higher than 20 to 80%, the temperature is maintained at 20 to 37° C., and the pH value is maintained at pH 3 to 8. Samples are taken at an interval of 2 to 10 hours and subjected to Western blot detection. Fermentation is stopped 5 to 90 hours after induction, and the fermentation broth is discharged. The fermentation broth is centrifuged using a refrigerated centrifuge, and then the cells are collected and stored at −20° C. The inducibly expressed HPV L1 protein can be self-assembled into virus-like particles (HPV L1 VLPs) inside *Pichia* yeast cell.

As said HPV L1 protein is expressed inside *Pichia* yeast cell, purer proteins can be obtained by performing cell disruption and protein purification and then allowed to be self-assembled into virus-like particles. Purification is generally performed as follows. The cells are washed to remove the attached medium components (salts, pigments, etc) in order to reduce their influence on subsequent purification. The washed cells are mixed into a suitable cell disruption buffer containing salt and surfactant components at certain concentrations. The salt components that can be used are for example NaCl and KCl at a concentration in the range of about 0.4 to 0.8 mol/l. The surfactant components that can be used are for example Tween-80, Tween-20 and Triton-X 100 at a concentration in the range of about 0.005 to 0.05% (w/v). The buffer systems that can be used are for example phosphate buffer, Tris buffer, MOPS buffer, and HEPES buffer at a concentration in the range of about 0.02 to 0.2 mol/l. The mixed cells can be disrupted using for example a high pressure homogenizer operating in a pressure range of about 800 to 2000 bars, achieving a disruption rate of greater than 90% in 2 to 4 disruption cycles, or a bead mill homogenizer using beads having diameters in the range of 0.2 to 0.4 mm which are loaded in an amount of about 70 to 90%, achieving a disruption rate of greater than 80% in 1 to 2 disruption cycles. The solution containing disrupted cells is subjected to high speed centrifugation at 6,000 to 10,000 rpm (SORVALL, HITACHI, etc.) for 20 to 60 minutes, or to tangential flow microfiltration using 0.45 to 0.65 μm membrane module (Millipore, PALL, etc.), in order to separate the supernatant and the precipitate, obtaining supernatant for further purification. The supernatant obtained can be subjected to anion exchange chromatography using such as Q Sepharose Flast Flow (GE) or DEAE SephroseFast Flow (GE) to remove some of the impurities in the supernatant, such as DNA, RNA and impurity proteins prior to conducting further purification. Alternatively, the supernatant obtained can be directly used to conduct further purification. For the further purification, the supernatant samples are loaded onto HPV L1 VLPs-adsorbable chromatographic media, such as SP Sepharose FF, Heparin SepharoseCL-6B (GE), Poros 50HS (Merck) and Fractogel@EMD TMAE-650 (Merck) to allow HPV L1 VLPs protein to efficiently bind to the chromatographic media. Then the media is washed using a salt concentration gradient (such as 0.5 to 1.0 M NaCl or KCl buffer solution) to separate impurities from HPV L1 VLPs protein. Subsequently, high concentration salt-containing buffer solution (such as 1.0 to 2.0 M NaCl or KCl buffer solution) is used to elute the bound HPV L1 VLPs protein, and the eluted preliminarily-purified HPV L1 VLPs protein is collected. Thus obtained preliminarily-purified HPV L1 VLPs protein is loaded onto chromatographic media for fine purification, such as CHT (BIO-RAD Type II), to which HPV L1 VLPs protein can efficiently bind under the conditions of a certain range of salt concentration (such as 0.3 to 1.5 M NaCl or KCl buffer solution). Then the media is eluted using a phosphate concentration gradient (such as a phosphate concentration in the range of 20 to 400 mM) to separate impurities from HPV L1 VLPs. Alternatively, the preliminarily-purified HPV L1 VLPs protein can also be loaded onto such chromatographic media for fine purification as Sephacryl S-1000 (GE) and HW-75 (TSK) to achieve the separation of impurities from HPV L1 VLPs protein through gel chromatography. The eluted HPV L1 VLPs protein after fine purification is collected as the final purified sample.

The purification method according to the present invention can remove most of the contaminating biomolecules (including DNAs, lipids and proteins). Detection using reduced SDS-PAGE electrophoresis or capillary electrophoresis (Beckman Coulter) revealed that the sample obtained by purification using POROS 50HS chromatography media had a purity of 75% to 80%, and the final HPV L1 VLPs protein sample purified using hydroxyapatite media had a purity of 90% to 95%. Western blot (Bio-RAD) detection showed specific staining reaction between target protein band and monoclonal or polyclonal antibody to HPV L1 VLPs. Dynamic light scattering detection (Malvern Instruments Zetasizer Nano ZS) showed that the purified sample had particles in a size range of about 50 to 80 nm, and transmission electron microscopy observation (Philips) revealed virus-like particles (VLPs) in the sample, with the particle size in the range of about 50 to 80 nm. In the present experiment, the hydroxyapatite media used is most preferably ceramic hydroxyapatite media filler with a particle size in the range of about 20 to 50 nm and a pore size of about 800 Å. The buffers used in chromatography have a pH in the range of 6 to 9, the preferable buffering system being 50 mM MOPS.

In comparison with the prior art, the present invention optimally designed a gene for HPV 18 L1 (full-length gene, or preferably truncated gene corresponding to HPV 18 L1 protein with deletions of 61 amino acids at the N-terminus) and cloned it into Pichia yeast such that a markedly increased expression of HPV 18 L1 protein was achieved compared with other expression systems (such as mammal cell, baculovirus, Saccharomyces cerevisiae). Following the expression, the virus-like particles obtained through purification were observed by electron microscopy to be 50-80 nm in size, similar to wild-type HPV particles. The virus-like particles assembled from recombinant HPV 18 L1 protein were adsorbed to an aluminium adjuvant and used to immune mice, generating high titers of anti-HPV 18 L1 antibodies. Neutralization experiment using pseudotype virus showed that the antibodies had very good neutralizing activity (that is, capable of inhibiting entry of pseudotype virus into cells). In addition, the optimally designed gene for HPV 16 L1 according to the present invention, after being cloned into Pichia yeast, resulted in a very high level of expression of HPV 16 L1 protein.

Immunogenic Macromolecule

The present invention also provides an immunogenic macromolecule having a diameter of 50 to 80 nm, which is a poly-molecular polymer essentially self-assembled from major capsid proteins L1 of human papilloma virus, said major capsid proteins L1 of human papilloma virus being expressed by Pichia yeast.

Preferably, the immunogenic macromolecule according to the present invention is prepared by the following method: (1) culturing said recombinant cell to allow said major capsid protein L1 of human papilloma virus to be expressed and to concurrently self-assemble into immunogenic molecules in the recombinant cells; (2) disrupting the cells obtained from step (1) to obtain supernatant containing the immunogenic molecules; and (3) successively purifying the supernatant obtained from step (2) using POROS 50 HS column chromatography and CHT column chromatography to obtain said immunogenic macromolecules.

The present invention also provides the use of said immunogenic macromolecule in the manufacture of a composition for the prevention or treatment of diseases related to human papilloma virus (HPV) infection. Said diseases are selected from, but not limited to, malignancies (such as cervical cancer, vaginal cancer, anal or perianal cancer, oropharyngeal cancer, maxillary sinus cancer, lung cancer) and cervical intraepithelial neoplasia.

Composition

The present invention also provides an immunogenic composition (such as a preventive or therapeutic vaccine) which comprises an effective amount of said immunogenic macromolecule according to the present invention and a pharmaceutically acceptable carrier.

The present invention also provides a method for preparing a vaccine against human papilloma virus, comprising preparing virus-like particles of recombinant human papilloma virus protein L1 using the method as described above, and then adding pharmaceutically acceptable vaccine adjuvant. Said vaccine adjuvant can be an aluminium adjuvant or other adjuvant. The virus-like particles formed from purified human papilloma virus protein (HPV L1), when adsorbed to an adjuvant, can be used as a vaccine.

As used herein, the term "pharmaceutically acceptable" component refers to a substance suitable for use in human and/or mammal subjects without undue adverse side effects (such as toxicity), commensurate with a reasonable benefit/risk ratio. The term "pharmaceutically acceptable carrier" refers to carriers for the administration of therapeutic agents, including various excipients and diluents. This teen refers to such carriers for therapeutic agents as are not per se the essential active components and are not unduly toxic after application. Suitable carriers are well-known to those of ordinary skill in the art. A full description of pharmaceutically acceptable carriers can be found in Remington's Pharmaceutical Sciences (Mack Pub. Co., N.J. 1991). The pharmaceutically acceptable carriers for the composition may comprise liquids, such as water, saline, glycerol and sorbitol. Moreover, these carriers may have auxiliary agents present, such as for example lubricating agent, glidant, wetting agent or emulsifying agent, pH buffering substance and stabilizing agent, e.g., albumin, or the like.

Said composition can be formulated into various dosage forms suitable for administration to mammals, including but not limited to injections, capsules, tablets, emulsions, and suppositories.

Animal experiments have showed that immunization of the animals with the vaccine prepared using the immunogenic macromolecule according to the present invention induced strong immune responses in the animals.

When intended for use, the immunogenic macromolecule according to the present invention is administered to the mammal subject (such as human subject) in a safe and effective amount, wherein said safe and effective amount is typically at least about 1 μg/kg body weight and is in most cases not more than about 10 mg/kg body weight, preferably in the range of about 1 μg/kg body weight to about 1 mg/kg body weight. The particular dosage administered is, of course, dependent on such considerations as the route of administration, the general health of the patient and the like, which are within the skill of medical practitioners.

The present invention is further described in conjunction with the following specific examples which should be understood to be illustrative of the present invention rather than limitative of the scope of the present invention. The experiment procedures in the following examples for which no particular conditions are specified generally follow those conditions such as described in Sambrook et. al., *Molecular Cloning: A Laboratory Manual*, New York, Cold Spring Harbor Laboratory Press, 1989), or those conditions recommended by the manufacturers. Unless otherwise indicated, the percentages and parts are by weight.

In the examples of the present invention, heat activated Pfu enzyme purchased from Stratagene Co., Ltd was used for DNA extension and PCR amplification.

In the examples of the present invention, pUC18 plasmid was purchased from Generay Biotech (Shanghai) Co., Ltd (Shanghai, China), and pPICZaB plasmid was purchased from Invitrogen Corp.

In the examples of the present invention, rabbit polyclonal antibodies to HPV18 L1 and HPV16 L1 proteins were prepared by Shanghai PrimeGene Bio-tech, LTD (Shanghai, China), MAB885 murine monoclonal antibody was purchased from CHEMICON Co., Ltd, and HRP labeled sheep anti-mouse IgG was purchased from Being Dingguo Changsheng Biotechnology Co., Ltd (Beijing, China).

In the examples of the present invention, BALB/c mice were purchased from Shanghai SLAC laboratory Animal Co., Ltd. (Shanghai, China).

In the examples of the present invention, the washing buffer used in the purification step comprises: 100 mM PB, 0.15 M NaCl, pH 7.0; The buffer used in cell disruption: 200 mM MOPS, 0.4 M NaCl, 0.05% Tween-80, pH 7.0;

Buffer E: 50 mM MOPS, 0.5 M NaCl, 0.05% Tween-80, pH 6.5;

Buffer F: 50 mM MOPS, 1.5 M NaCl, 0.05% Tween-80, pH 6.5;

Buffer G: 50 mM MOPS, 0.6M NaCl, 0.05 M PB, 0.05% Tween-80, pH 6.5;

Buffer H: 0.6M NaCl, 200 mM PB, 0.05% Tween-80, pH 6.5.

EXAMPLE 1

Design and Synthesis of Codon-Optimized Gene for HPV 18 L1

1.1. Design of Codon-Optimized Gene for HPV 18 L1

The present invention relates to DNA molecules encoding the major capsid protein L1 of human papilloma virus subtype 18 (HPV18), which have been codon-optimized with codons preferred by *Pichia* yeast. Three DNA sequences, which are as set forth in SEQ ID NO: 4, 5 and 6, respectively, were obtained through optimization of codons and alteration of optimized codons, as detailed below.

Firstly, through repeated experiments, modifications were made on the naturally-occurring gene encoding HPV 18L1 by optimizing the codons for all the corresponding amino acids of the gene to design a novel HPV DNA sequence, that is, SEQ ID NO:4.

Then, in order to avoid the presence of a high GC ratio in the transcribed mRNAs, the influence of mRNA secondary structure on the efficiency of translation, and the occurrence of common restriction sites, alterations were made to the optimized codons, such as, the codon for asparagine (Asn) being altered from AAC to AAT, the codon for lysine (Lys) being altered from AAG to AAA, the codon for aspartic acid (Asp) being altered from GAT to GAC, the codon for phenylalanine (Phe) being altered from TTT to TTC, the codon for tyrosine (Tyr) being altered from TAC to TAT, and the codon for glycine (Gly) being altered from GGT to GGA, thus obtaining two altered, novel HPV DNA sequences: SEQ ID NO: 5, which was altered from SEQ ID NO: 4 through alterations to the codons for asparagine (Asn), lysine (Lys) and aspartic acid (Asp); and SEQ ID NO: 6, which was altered from SEQ ID NO: 4 through alterations to the codons for phenylalanine (Phe), tyrosine (Tyr) and glycine (Gly).

1.2. Synthesis of Codon-Optimized Gene for HPV 18 L1

The codon-optimized gene for HPV 18 L1 as set forth in SEQ ID NO: 4 was synthesized and used as template to perform PCR amplification using primers a1 and a2 which have the following sequences:

```
                                      (SEQ ID NO: 12)
a1:    5'-ATAGAATTCAAGATGTGTTTGTACACTAGAGTTT-3';

(SEQ ID NO: 13)
a2:    5'-AATGGTACCCTATTACTTTCTAGCTCTAACT-3'.
```

The PCR products obtained were subjected to separation by agarose gel electrophoresis and the target sequence was recovered from the gel, obtaining a fragment about 1.7 kb in size. This fragment was sequenced, with the result of sequencing as shown in SEQ ID NO: 4, and was demonstrated from the result to be the full-length codon-optimized gene for HPV 18L1. Thus obtained gene for HPV 18L1, by virtue of the EcoRI and KpnI restriction sites on its ends, was ligated into pUC18 plasmid (available from Generay Biotech (Shanghai) Co., Ltd (Shanghai, China)). The resulting construct was verified by sequencing to be correct, and was named as pUC-18L1.

Codon-optimized genes for HPV 18L1 as shown in SEQ ID NO: 5 and 6 were obtained in a similar procedure as above mentioned.

In order to verify the feasibility of the optimized sequences, one of the codon-optimized genes for HPV 16L1 obtained in this Example 1 (SEQ ID NO: 4) was exemplarily used to construct an expression plasmid to assess for its expression, as detailed in Example 2.

EXAMPLE 2

Construction of Expression Vector of HPV 18L1 Gene

The optimized sequence of SEQ ID NO: 4 was cloned into Pichia yeast expression vector, as depicted in FIG. 1 and as detailed in the following steps.

2.1. The forward and reverse primers having the following sequences, which were required for amplifying HPV 18L1 gene, were synthesized:

```
forward primer:
                                      (SEQ ID NO: 14)
5'-TCCCAATCTTCGAAACGATGTGTTTGTACACTAGAGTTT-3';

reverse primer:
                                      (SEQ ID NO: 13)
5'-AATGGTACCCTATTACTTTCTAGCTCTAACT-3';
```

Wherein the forward primer comprises a BstBI restriction site, and the reverse primer comprises a KpnI restriction site flanking the termination codon, said restriction sites respectively as shown in the underlined portions of the primer sequences above.

Figure 2:
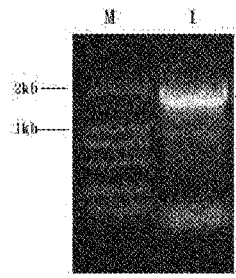
FIG. 2 is a diagram of PCR amplification of the gene for HPV 18L1.

2.2. PCR amplification was performed using the above primers and using the pUC-18L1 obtained in Example 1 as template. The amplified product was detected by electrophoresis, with the result being shown in FIG. 2, demonstrating that a full-length codon-optimized gene for HPV 18L1 was obtained. The PCR amplified fragment was digested with BstBI and KpnI (restriction endonucleases) and then ligated with pPICZaB (Invitrogen Corp.) which was also digested with BstBI and KpnI. Then, the ligated construct was used to transform competent cells of *E. coli* Top10 strain (available from Generay Biotech (Shanghai) Co., Ltd (Shanghai, China)), and the transformed cells were plated onto LB agar containing 25 µg/ml of zeocin.

Figure 3:
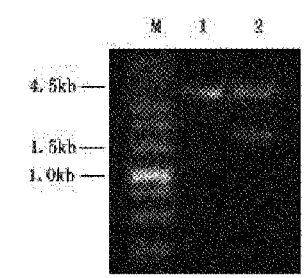
FIG. 3 is a diagram of identification of pPICZ-18L1 vector, wherein lane 1 represents BstBI- and KpnI-digested pPICZαB; and lane 2 represents BstBI- and KpnI-digested pPICZ-18L1.

The transformed cells were able to grow on LB media containing zeocin as the pPICZaB vector carried zeocin-resistance gene. Single colonies of the transformed cells were separated to prepare plasmid DNA. HPV 18L1 gene and vector sequence were detected through restriction mapping (see FIG. 3) and nucleotide sequence analysis to identify the correct construct comprising HPV 18L1 gene, which was named pPICZ-18L1. As secretion signal (a-factor signal) has been cleaved from the constructed plasmid, HPV 18L1 protein should be intracellularly expressed protein.

EXAMPLE 3

Construction and Expression of HPV 18L1 Gene-Expressing Strain 3.1. Construction of HPV 18L1 Gene-Expressing Strain pPICZ-18L1 plasmid was linearized with a restriction endonuclease enzyme SacI, and empty plasmid pPICZaB was likewise digested with SacI to serve as negative control. The enzyme digestion solution was added with absolute ethanol to obtain DNA precipitate. The linearized pPICZ-18L1 fragment was dissolved with a small amount of double-distilled water and used to transform *Pichia* yeast strain X-33 (Invitrogen Corp.) by electroporation under the following conditions: DNA fragment, 5 µg; voltage, 1,500 volts; resistance, 25 omhs; electroporation time, 5 milliseconds. The electroporated cells were plated onto YPDS agar containing 200 µg/ml zeocin. As the pPICZaB vector carried zeocin-resistance gene, the transformed cells were able to grow on YPDS media containing zeocin. Single colonies of transformed cells were isolated, thus obtaining HPV 18L1 gene-expressing *Pichia* yeast strain.

3.2. Expression of HPV 18L1 Gene-Expressing *Pichia* Yeast Strain

Figure 4:
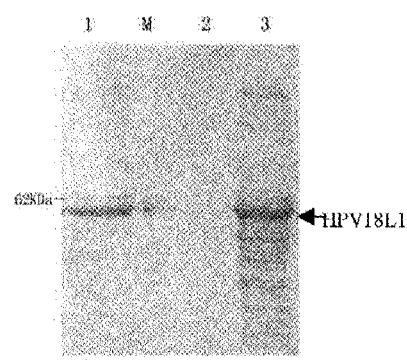
FIG. 4 is a diagram of Western blot identification of the expression of HPV 18 L1, wherein M represents Rainbow Marker (Fermentas Co., Ltd); 1 represents the positive control of expression; 2 represents the negative control of expression; and 3 represents the strain expressing HPV18L1. The arrow designates the expressed HPV 18 L1.

The obtained HPV 18L1 gene-expressing *Pichia* yeast strain was plated onto resistance plates containing 1,000 µg/ml or 1,500 µg/ml zeocin. Clones obtained from plates having high concentration of resistance were separately cultured in 4 mL of YPD liquid culture media for 24 hours followed by induction of gene expression in BMMY culture media for 48 hours. Then cells were harvested by centrifugation and some of the cells were disrupted to obtain supernatant for performing Western blotting identification. The result of identification is shown in FIG. 4, which indicated the presence of HPV 18L1 protein in the supernatant.

Although SEQ ID NO: 4 sequence was used for cloning and expression in Examples 2 and 3 of the present invention, it will be obvious to those skilled in the art that similar results can be obtained when SEQ ID NO: 5 and 6 sequences are used for cloning and expression, and therefore these two sequences are also within the scope of the present invention. Moreover, those skilled in the art will, in light of the spirit of the present invention, readily construct similar sequences and clone and express the constructed sequences in. *Pichia* yeast to obtain similar or better results, and therefore these sequences are also deemed to be within the scope of the present invention.

EXAMPLE 4

Purification of HPV 18L1 Protein

The cells prepared in Example 3 were disrupted and centrifuged, and the resulting supernatant was subjected to purification by chromatography to obtain HPV 18L1 protein which has self-assembled into virus-like particles, as detailed below.

HPV 18L1 gene-expressing *Pichia* yeast cells were mixed with washing buffer in a ratio of 1:3 and shaken well, and the mixture was centrifuged at 8,000 rpm for 5 minutes to collect the cells. The above procedure was repeated twice.

The washed cells were mixed with cell disruption buffer in a ratio of 1:5 and shaken well, and the cells in the resulting suspension were disrupted under high pressure. The above procedure was repeated so that 90% of the cells were disrupted. The resulting disrupted cell solution was centrifuged at 9,000 rpm at 10° C. for 30 minutes and the supernatant was collected.

The supernatant obtained was preliminarily purified on POROS 50HS (Applied Biosystems Co., Ltd) chromatography column by eluting with a linear gradient of 100% buffer E to 100% buffer F and collecting the elution fractions. Sample was taken from the purified elution fractions and reduced to form monomeric proteins for detection by SDS-PAGE and Western blotting.

The elution fractions containing HPV 18L1 protein were combined and subjected to fine purification on CHT (BIO-RAD Type II) chromatography column eluted with a linear gradient of 100% buffer G to 100% buffer H. The elution fractions were collected, from which sample was taken and reduced to form monomeric proteins for detection by SDS-PAGE and Western blotting. The elution fractions containing HPV 18L1 protein were combined, thereby obtaining the final purified sample with a purity of greater than 90%.

EXAMPLE 5

Preparation of HPV 18L1 Vaccine

The purified HPV 18L1 protein obtained in Example 4 above was adsorbed to an aluminium adjuvant to prepare an immunogenic HPV 18L1 vaccine according to the method described in *Chinese Pharmacopoeia* (2005 edition).

EXAMPLE 6

Determination of Immunogenicity of the Expression Product of HPV 18L1 Gene

Twenty-four 6 to 8 weeks old SPF BALB/c mice were divided into 4 groups, with 6 mice in each group. Mice in the first group (as the negative control group) were immunized by cutaneous injection of 0.1 mL of aluminium adjuvant-containing buffer (0.32 M sodium chloride, 0.35 mM sodium borate, 0.01% Tween-80, 0.01 M histidine, pH 6.5) for three times on days 0, 7 and 21 respectively, and mice in the other three groups (as the test groups) were similarly immunized with 0.1 mL of aluminium adjuvant-adsorbed VLPs at a concentration of 5 µg/mL, 0.5 µg/mL and 0.05 µg/mL respectively. Blood samples were collected two weeks after the third immunization. The blood samples collected were stood at 37° C. for 2 hours and then centrifuged at 4,000 g for 10 minutes. The supernatant, which was obtained as mouse polyclonal antiserum, was aspirated and stored at −20° C. Additionally, the supernatant was assayed for seroconversion rate and titer, as detailed below.

6.1. Detection of Seroconversion Rate

The purified HPV 18L1 protein expressed by *Pichia* yeast was diluted with coating solution to 1 µg/mL. An aliquot of 0.1 mL of the dilution was added into each well of an ELISA plate, and the plate was incubated at 4° C. overnight. The coating solution was removed from each well, which was then washed with 0.3 mL of PBST. Then, each well was blocked by incubating with 0.3 mL of blocking solution (5% skimmed milk powder+PBST) at 37° C. for 2 hours. Each well was added with 0.1 mL of test sera (serum obtained from mice immunized with aluminium adjuvant-adsorbed HPV 18L1 protein and serum obtained from mice immunized with aluminium adjuvant alone) solution obtained by diluting the sera with dilution buffer (2% skimmed milk powder-1-PBST) in a ratio of 1:400, and then incubated at 37° C. for 1 hour. Then the test sera solution was removed and each well was washed with 0.3 mL of washing buffer. Subsequently, each well was added with 0.1 mL of HRP labeled goat anti-mouse IgG obtained by diluting the IgG with dilution buffer in a ratio of 1:5,000 and incubated at 37° C. for 0.5 hour. Then the ELISA solution was removed and each well was washed with 0.3 mL of washing buffer. Then, each well was added with 0.1 mL DAB color development solution, and interaction was allowed to occur in dark at room temperature for 20 minutes. Afterwards, 0.05 mL of 2 M $H_2SO_4$ stop solution was added to each well to stop the reaction, and $OD_{450}$ value was determined using an ELISA reader, with the readings shown in Table 2 below.

TABLE 2

| | $OD_{450}$ readings | | | | | |
|---|---|---|---|---|---|---|
| | Mouse 1 | Mouse 2 | Mouse 3 | Mouse 4 | Mouse 5 | Mouse 6 |
| 5 µg immunization group | 1.231 | 1.208 | 1.229 | 1.208 | 1.106 | 1.666 |
| 0.5 µg immunization group | 1.150 | 1.244 | 1.227 | 1.158 | 1.252 | 1.171 |
| 0.05 µg immunization group | 1.424 | 0.357 | 1.182 | 1.101 | 1.164 | 2.448 |
| Aluminium adjuvant group | 0.087 | 0.204 | 0.155 | 0.113 | 0.143 | 0.100 |
| Cutoff value | 0.263 | | | | | |

The Cutoff value is the sum of the average of the $OD_{450}$ values of antibody to test serum of negative control (mouse serum obtained from immunization with aluminium adjuvant) plus three times the standard deviation. Mouse with an $OD_{450}$ value greater than the Cutoff value was regarded as positive, and mouse with an $OD_{450}$ value lower than the Cutoff value was regarded as negative. The results of seroconversion rate for the three test groups are shown in Table 3 below.

TABLE 3

| | Results of seroconversion rate | | |
|---|---|---|---|
| | 5 µg/mL immunization group | 0.5 µg/mL immunization group | 0.05 µg/mL immunization group |
| Seroconversion rate | 100% | 100% | 100% |

6.2. Determination of Sera Titers

The purified HPV 18L1 protein was diluted with coating solution to 1 µg/mL. An aliquot of 0.1 mL of the dilution was added into each well of an ELISA plate, and the plate was incubated at 4° C. overnight. The coating solution was removed from each well, which was then washed with 0.3 mL of PBST. Then, each well was blocked by incubating with 0.3 mL of blocking solution (5% skimmed milk powder+PBST) at 37° C. for 2 hours. The test sera (sera obtained from mice immunized with HPV 18L1 protein) was serially double diluted with dilution buffer (2% skimmed milk powder+PBST) from 1:500 dilution to 1:32,000 dilution, while the negative control serum (serum obtained from mice immunized with aluminium adjuvant) was diluted in a ratio of 1:10,000. Each well was added with an aliquot of 0.1 mL of diluted serum (test serum or negative control serum) and incubated at 37° C. for 1 hour. Then the test serum solution was removed and each well was washed with 0.3 mL of washing buffer. Subsequently, each well was added with 0.1 mL of HRP labeled sheep anti-mouse IgG obtained by diluting the IgG with dilution buffer in a ratio of 1:5,000, and incubated at 37° C. for 0.5 hour. Then the ELISA solution was removed and each well was washed with 0.3 mL of washing buffer. Then, each well was added with 0.1 mL DAB color development solution, and interaction was allowed to occur at room temperature for 20 minutes. Afterwards, 0.05 mL of 2

M $H_2SO_4$ stop solution was added to each well to stop the reaction, and $OD_{450}$ value was determined using an ELISA reader.

Sera titers were calculated by end point titration method, with the results shown in Table 4 below.

TABLE 4

Results of titer determination

| | Mouse 1 | Mouse 2 | Mouse 3 | Mouse 4 | Mouse 5 | Mouse 6 |
|---|---|---|---|---|---|---|
| 5 μg immunization group | 8383 | 1315490 | 896331 | 2029474 | 43088 | 23781 |
| 0.5 μg immunization group | 1154285 | 342344 | 415340 | 149924 | 1003880 | 103784 |
| 0.05 μg immunization group | 24237 | 1000 | 306880 | 341405 | 564089 | 27950 |

In summary, as shown in Examples 1-6, the gene for major capsid protein L1 of human papilloma virus subtype 18, as provided by the present invention, is an optimized HPV 18L1 gene, which has the advantages of being more suitable for efficiently expressing target protein in yeast host and meeting the requirements of industrial production. Moreover, the HPV 18L1 vaccine as provided by the present invention, which was prepared from adjuvant-adsorbed purified VLPs (virus-like particles self-assembled from HPV 18L1 protein), was demonstrated to be strongly immunogenic in mice as determined by seroconversion rate and serum titer. Further, said method has the advantages of low cost, high yield and more uniform and stable quality of products due to the use of *Pichia* yeast expression system.

EXAMPLE 7

Design and Synthesis of Codon-Optimized Gene for Truncated HPV 18 L1

7.1. Design of Codon-Optimized Gene for Truncated HPV 18 L1

The present invention relates to DNA molecules encoding the truncated major capsid protein L1 of human papilloma virus subtype 18 (HPV18), which have been codon-optimized with codons preferred by *Pichia* yeast. Three DNA sequences, which are as set forth in SEQ ID NO: 1, 2 and 3, respectively, were obtained through optimization of codons, alteration of optimized codons and truncation of 61 amino acids from the N terminus, as detailed below.

Firstly, modifications were made on the naturally-occurring gene encoding HPV 18L1 in a similar manner as in Example 1 above to design a novel HPV DNA sequence.

Then, in order to avoid the presence of a high GC ratio in the transcribed mRNAs, the influence of mRNA secondary structure on the efficiency of translation, and the occurrence of common restriction sites, alterations were made to the optimized codons, such as, the codon for asparagine (Asn) being altered from AAC to AAT, the codon for lysine (Lys) being altered from AAG to AAA, the codon for aspartic acid (Asp) being altered from GAT to GAC, the codon for phenylalanine (Phe) being altered from TTT to TTC, the codon for tyrosine (Tyr) being altered from TAC to TAT, and also 61 amino acids were truncated from the N terminus, thus obtaining three novel truncated HPV DNA sequences, wherein:

SEQ ID NO: 1 is the DNA sequence without codon alteration;

SEQ ID NO: 2 is the DNA sequence obtained from SEQ ID NO: 1 by altering the codons for asparagine (Asn), lysine (Lys) and aspartic acid (Asp);

SEQ ID NO: 3 is the DNA sequence obtained from SEQ ID NO: 1 by altering the codons for phenylalanine (Phe), tyrosine (Tyr) and glycine (Gly).

7.2. Synthesis of Codon-Optimized Gene for Truncated HPV 18 L1

The full-length codon-optimized gene for truncated HPV 18 L1, as set forth in SEQ ID NO: 1 was obtained using essentially the same method as described in Example 1 above mentioned. Thus obtained gene for truncated HPV18L1, by virtue of the EcoRI and KpnI restriction sites on its ends, was ligated into pUC18 plasmid (available from Generay Biotech (Shanghai) Co., Ltd (Shanghai, China)). The resulting construct was verified by sequencing to be correct, and was named as pUC-18L1'.

The codon-optimized genes for truncated HPV 18 L1, as set forth in SEQ ID NO: 2 and 3, were obtained in a similar method.

In order to verify the feasibility of the optimized sequences, one of the codon-optimized genes for truncated HPV 18L1 obtained in this Example 7 (SEQ ID NO: 1) was exemplarily used to construct an expression plasmid to assess for its expression, as detailed in Example 8.

EXAMPLE 8

Construction of Expression Vector of Truncated HPV 18L1 Gene

The optimized sequence of SEQ ID NO: 1 was cloned into *Pichia* yeast expression vector, as detailed in the following steps.

8.1. The forward and reverse primers having the following sequences, which were required for amplifying HPV 18L1 gene, were synthesized:

```
forward primer:
                                    (SEQ ID NO: 15)
5'-TCCCAATCTTCGAAACGATGGCTTTGTGGA-3';

reverse primer:
                                    (SEQ ID NO: 13)
5'-AATGGTACCCTATTACTTTCTAGCTCTAACT-3'.
```

Wherein the forward primer comprises a BstBI restriction site, and the reverse primer comprises a KpnI restriction site flanking the termination codon, said restriction sites respectively as shown in the underlined portions of the primer sequences above.

Figure 5:
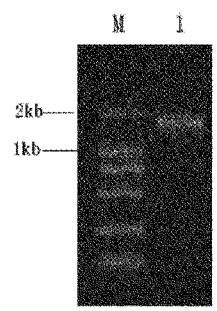
FIG. 5 is a diagram of PCR amplification of the gene for truncated HPV 18L1.

8.2. PCR amplification was performed using the above primers and using the pUC-18L1' obtained in Example 7 as template. The amplified product was detected by electrophoresis, with the result being shown in FIG. 5, demonstrating that a full-length codon-optimized gene for truncated HPV 18L1 was obtained. The PCR amplified fragment was digested with BstBI and KpnI (restriction endonucleases) and then ligated with pPICZaB (Invitrogen Corp.) which was also digested with BstBI and KpnI. Then, the ligated construct was used to transform competent cells of *E. coli* Top10 strain (available from Generay Biotech (Shanghai) Co., Ltd (Shanghai, China)), and the transformed cells were plated onto LB agar containing 25 µg/ml of zeocin.

Figure 6:
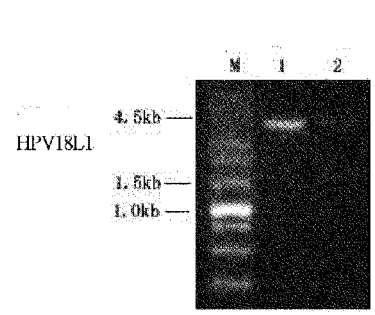
FIG. 6 is a diagram of identification of pPICZ-18L1' vector, wherein lane 1 represents BstBI- and KpnI-digested pPICZαB, and lane 2 represents BstBI- and KpnI-digested pPICZ-18L1'.

The transformed cells were able to grow on LB media containing zeocin as the pPICZaB vector carried zeocin-resistance gene. Single colonies of the transformed cells were separated to prepare plasmid DNA. HPV 18L1 gene and vector sequence were detected through restriction mapping (see FIG. 6) and nucleotide sequence analysis to identify the correct construct comprising truncated HPV 18L1 gene, which was named pPICZ-18L1'. As secretion signal (a-factor signal) has been cleaved from the constructed plasmid, therefore the HPV 18L1 protein expressed should be intracellularly expressed protein.

EXAMPLE 9

Construction and Expression of Truncated HPV 18L1 Gene-Expressing Strain 9.1. Construction of Truncated HPV 18L1 Gene-Expressing Strain pPICZ-18L1' plasmid was linearized with a restriction endonuclease enzyme SacI, and empty plasmid pPICZaB was likewise digested with SacI to serve as negative control. The enzyme digestion solution was added with absolute ethanol to obtain DNA precipitate. The linearized pPICZ-18L1' fragment was dissolved with a small amount of double-distilled water and used to transform *Pichia* yeast strain X-33 (Invitrogen Corp.) by electroporation under the following conditions: DNA fragment, 5 µg; voltage, 1,500 volts; resistance, 25 omhs; electroporation time, 5 milliseconds. The electroporated cells were plated onto YPDS agar containing 200 µg/ml zeocin (from Zeocin Co.). As the pPICZaB vector carried zeocin-resistance gene, the transformed cells were able to grow on YPDS media containing zeocin. Single colonies of transformed cells were isolated, thus obtaining truncated HPV 18L1 gene-expressing *Pichia* yeast strain.

9.2. Expression of Truncated HPV 18L1 Gene-Expressing *Pichia* Yeast Strain

Figure 7:
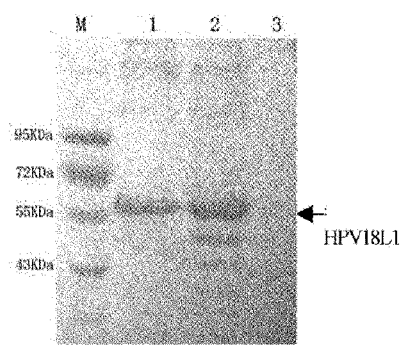
FIG. 7 is a diagram of Western blot identification of the expression of truncated HPV 18 L1, wherein M represents Rainbow Marker (Fermentas Co., Ltd); 1 represents the positive control of expression; 2 represents the strain expressing truncated HPV18L1; and 3 represents the negative control of expression. The arrow designates the expressed truncated HPV 18 L1.

The obtained truncated HPV 18L1 gene-expressing *Pichia* yeast strain was plated onto resistance plates containing 1,000 µg/ml or 1,500 µg/ml zeocin. Clones obtained from plates having high concentration of resistance were separately cultured in 4 mL of YPD liquid culture media for 24 hours followed by induction of gene expression in BMMY culture media for 48 hours. Then cells were harvested by centrifugation and some of the cells were disrupted to obtain supernatant for performing Western blotting identification. The result of identification is shown in FIG. 7, which indicated the presence of truncated HPV 18L1 protein in the supernatant.

Although SEQ ID NO: 1 sequence was used for cloning and expression in Examples 8 and 9 of the present invention, it will be obvious to those skilled in the art that similar results can be obtained when SEQ ID NO: 2 and 3 sequences are used for cloning and expression, and therefore these two sequences are also within the scope of the present invention. Moreover, those skilled in the art will, in light of the spirit of the present invention, readily construct similar sequences and clone and express the constructed sequences in *Pichia* yeast to obtain similar or better results, and therefore these sequences are also deemed to be within the scope of the present invention.

EXAMPLE 10

Large-Scale Expression and Detection of Truncated HPV 18L1 Protein

1. Large-Scale Expression of Recombinant Truncated HPV 18L1 Protein

Preparation of inoculum solution: One glycerol freezing tube of recombinant yeast stock was taken from working cell bank. After thawing, 100 µL of the stock was inoculated into 5 mL of YPD media and cultured at 280 rpm at 30° C. for 20 hours, at which time $OD_{600}$ was detected to be 1 to 2 and no contamination from other microorganisms was microscopically observed. 1 mL of the activation fluid (which has been tested to be satisfactory) was inoculated into 500 mL of YPD media and cultured at 280 rpm at 30° C. for 20 hours, at which time $OD_{600}$ was detected to be 2 to 6 and no contamination from other microorganisms was microscopically observed.

Process of fermentation: Basal salt medium for fermentation was prepared using deionized water: $BSM_1$ ($K_2SO_4$ 273 g, $MgSO_4$ 109 g, $CaSO_4.2H_2O$ 17.6 g, $H_3PO_4$ 400.5 mL, KOH 62 g, glycerol 600 g, $PTM_1$ 60 mL, defoamer 1 mL; add deionized water to a volume of 15 L). The prepared medium, which contained no antibiotics, was transferred into a 30 L fermentation tank (Bioengineering Co., Ltd) and sterilized in the tank at 121° C. for 30 minutes, followed by cooling to 30° C. The inoculum solution previously prepared was used to inoculate the sterilized medium in a ratio of 1:15. Fermentation was started at a temperature of 30.0±0.5° C., an initial pH of 5.00±0.05, an initial stirring speed of 300 rpm, an aeration volume of 0.5 vvm and a dissolved oxygen (DO) of 100%, with addition of trace salts $PTM_1$ ($CuSO_4.5H_2O$ 6.0 g, NaI 0.008 g, $MnSO_4$ 3.0 g, $NaMoO_4$ 0.2 g, $H_3BO_3$ 0.02 g, $ZnSO_4$ 20.0 g, $CoCl_2$ 0.5 g, $FeSO_4.7H_2O$ 65.0 g, biotin 0.2 g, and $H_2SO_4$ 5.0 mL; add deionized water to a volume of 1 L). The initial proliferation stage lasted for about 20 hours, during which time the dissolved oxygen was maintained at no lower than 30%. When the carbon source was completely consumed, the dissolved oxygen increased rapidly, at which time the wet cell weight was up to about 100 g/L. In the initial two hours, the fermentation was supplemented with 50% (v/v) glycerol solution (added with 12 mL of $PTM_1$ per liter) at a rate of 200 mL/h. Then the supplementation was continued at a rate of 300 mL/h for about 8 hours, during which time the dissolved oxygen was maintained at higher than 20% by adjusting the stirring speed, air flow and tank pressure (<0.8 bar). When the wet cell weight reached about 350 g/L, supplementation was stopped, and the dissolved oxygen increased accordingly. Meanwhile, the pH value was adjusted to 6.00±0.05, and methanol (added with 12 mL of $PTM_1$ per liter) was added at an initial addition rate of 30 mL/h to induce gene expression. The addition rate of methanol was increased slowly until a set rate of 90 mL/h after 4 hours. During induction, the dissolved oxygen was maintained at higher than 20% (v/v), the temperature at 30° C. and the pH at 6.00±0.05. Sample was taken every eight hours and subjected to Western blotting detection. Forty-eight hours after induction, the fermentation completed and the fermentation broth was discharged.

Harvest of cells: The fermentation broth was centrifuged using a cryo-centrifuge to collect the cells, which were then weighed. The batch number, date and weight for the recovered cells were recorded, and the cells were sent for purification or stored at −20° C.

2. Detection

The purified (according to the method described in Example 11 below) truncated HPV 18L1 protein was used to prepare a protein concentration standard curve. With cells before induction as negative control, the expression amount of HPV 18L1 gene in *Pichia* yeast during fermentation was detected using sandwich ELISA method, as detailed below.

Rabbit polyclonal antibody to HPV 18L1 protein was diluted 2,000 fold with coating solution. An aliquot of 0.1 mL of the diluted rabbit polyclonal antibody was added to each well of an ELISA plate, and the plate was incubated at 4° C. overnight. Then the coating solution was removed from each well, which was then washed with 0.3 mL of PBST. Then, each well was blocked by incubating with 0.3 mL of blocking solution at 37° C. for 2 hours.

The purified HPV 18L1 protein was gradiently diluted with dilution buffer from a concentration of 2 µg/mL to 0.0625 µg/mL. Meanwhile, the supernatant obtained from disrupted fermentation broth was diluted 200 fold. Then, for each of the HPV 18 L1 protein solutions of different concentrations obtained by the serial dilution and for the diluted supernatant, an aliquot of 0.1 mL was taken and added to a separate well of the above-treated ELISA plate, and the plate was incubated at 37° C. for 1 hour. After incubation, the aliquot of antigen solution was removed from each well, which was then washed with 0.3 mL of washing buffer. Then, MAB885 mouse monoclonal antibody (purchased from CHEMICON Co., Ltd) was diluted 1,000 fold with dilution buffer, and an aliquot of 0.1 mL of the dilution was added to each well and incubated at 37° C. for 1 hour. Following incubation, the monoclonal antibody solution was removed from each well, which was then washed with 0.3 mL of washing buffer. Subsequently, each well was added with 0.1 mL of HRP labeled goat anti-mouse IgG obtained by diluting the IgG 5,000-fold with dilution buffer, and incubated at 37° C. for 0.5 hour. Then the ELISA solution was removed and each well was washed with 0.3 mL of washing buffer. Then, each well was added with 0.1 mL DAB color development solution, and interaction was allowed to occur at room temperature for 20 minutes. Afterwards, 0.05 mL of 2 M $H_2SO_4$ stop solution was added to each well to stop the reaction, and $OD_{450}$ value was determined using an ELISA reader.

The $OD_{450}$ values for the gradiently diluted solutions of HPV 18L1 protein were used to prepare a protein concentration standard curve. Using this standard curve, the expression amount of truncated HPV 18L1 protein during fermentation was obtained, as shown in Table 5 below.

Particularly speaking, the purified target protein stock solution with known concentrations was serially diluted into solutions of a range of concentrations, such as 2 µg/mL, 1 µg/mL, 0.5 µg/mL, 0.25 µg/mL and 0.125 µg/mL, which were used as standard concentrations. ELISA detection was conducted on these solutions to obtain the corresponding $OD_{450}$ values. Then a standard linear regression equation was generated, with the ordinate representing the concentration and the abscissa representing the $OD_{450}$ value.

The supernatant obtained from the disrupted fermentation broth was serially diluted, such as being diluted 50 fold, 100 fold, 200 fold and 400 fold. $OD_{450}$ values were detected for these serial dilutions, and the corresponding concentrations (µg/mL) were found from the standard linear regression equation. The concentration of the target protein in the supernatant (µg/mL) was then calculated by multiplying the found concentration with the corresponding dilution factor. As the disrupted broth was prepared from wet cell weight:cell disruption buffer=1:5, therefore the expression amount of the target protein in the wet cells (µg/g wet cells) was 5× the concentration of the target protein in the supernatant (µg/mL). And the concentration of expression of the target protein in the fermentation broth (µg/L fermentation broth) was obtained by multiplying the above-obtained expression amount of the target protein in the wet cells with the density of cells in the fermentation broth (g wet cells/L fermentation broth).

Concentration of the target protein in the supernatant obtained from the disrupted fermentation broth (µg/mL)=Dilution factor×Concentration of standard target protein concentration (µg/mL)×$OD_{450}$ (supernatant obtained from the disrupted fermentation broth)/$OD_{450}$ (standard target protein concentration);

Concentration of the expressed target protein in the fermentation broth (µg/L fermentation broth)=5× Concentration of the target protein in the supernatant obtained from the disrupted fermentation broth (µg/mL)×Density of cells in the fermentation broth (g wet cells/L fermentation

TABLE 5

Detection of expression amount of truncated HPV 18 L1 gene in *Pichia* yeast during fermentation

| Sample | Dilution factor | $OD_{450}$ | Concentration of stock solution (µg/mL) | Average concentration (µg/mL) | Converted concentration | Fermentation density | Expression amount during fermentation |
|---|---|---|---|---|---|---|---|
| Disrupted fermentation broth | 200 | 0.455 | 161.4 | 176 | 880 µg/g wet cells | 438 g/L | 385 mg/L fermentation broth |
| Supernatant 1 | 100 | 0.718 | 185.6 | | | | |
| Disrupted fermentation broth | 200 | 0.365 | 153.0 | 152 | 760 µg/g wet cells | 413 g/L | 314 mg/L fermentation broth |
| Supernatant 2 | 100 | 0.612 | 160.5 | | | | |
| Negative control | 100 | 0.091 | | | | | |
| Blank control | — | 0.083 | | | | | |

It can be seen from the results shown in Table 5 that, the optimized sequence of the gene for HPV 18L1 protein according to the present invention not only can be expressed into HPV 18L1 protein in *Pichia* yeast, but also has a high expression amount, meeting the requirements of industrial production.

EXAMPLE 11

Purification of Truncated HPV 18L1 Protein

Cleaning:
The above-obtained *Pichia* yeast cells expressing truncated HPV 18 L1 protein, which had been stored at −20° C., was thawed at room temperature. Then the thawed cells were mixed with washing buffer (100 mM PB, pH 7.0, 0.15 M NaCl) or water for purification in a ratio of 1:3 (g/mL), and completely homogenized with the buffer or water in a homogenizer (FLUKO). Subsequently, the homogenate was subjected to high speed centrifugation (SORVALLRC6PLUS) at 8000 rpm for 5 minutes to separate the cells, the supernatant being decanted. The above procedure was repeated twice, thereby achieving the cleaning of the cells.

Disruption:
The cleaned cells were added and mixed into cell disruption buffer (100 mM MOPS, 0.75M NaCl, 0.05% Tween-80, pH 7.0) in a ratio of 1:5 (g/mL), and completely homogenized with the buffer in a homogenizer (FLUKO). The cells suspended in the homogenate were subjected to disruption using a high-pressure homogenizer (ATSAH110B) operating at a pressure in the range of 1200 to 1300 bars. This disruption was repeated four times, and then the disrupted cell solution was discharged at 4 to 8° C., with 90% of the cells being disrupted.

Clarification:
The disrupted cell solution obtained by high-pressure disruption as above was poured into a centrifugation cup and centrifuged at high speed to remove cell debris, obtaining supernatant for subsequent column chromatography separation. The centrifuge used is SORVALLRC6PLUS, rotor model: FIBERLITEF10-6x500y, centrifugation setting: 9,000 rpm, 30 min, 10° C.

Preliminary Purification:
Chromatography media POROS 50HS (Applied Biosystems) was loaded into a chromatography column (diameter 26 mm, height 10, volume 50 mL). Preliminary purification was conducted in the following steps: (1) washing and disinfection: the column was washed with two column volumes of 0.5 M NaOH; (2) regeneration and equilibration: the column was washed with two column volumes of Buffer F and then equilibrated with Buffer E; (3) loading sample: the supernatant obtained by centrifuging the disrupted cell solution as above was loaded onto the column; (4) rinsing: the column was rinsed with five column volumes of Buffer E until the baseline stabilized; (5) elution: the column was eluted with a linear gradient of 100% Buffer E to 100% Buffer F in a total elution volume of six column volumes; and (6) collection: the chromatographic peaks having a conductivity in the range of 70 to 100 ms/cm were collected and stored at 4° C.

Figure 8:
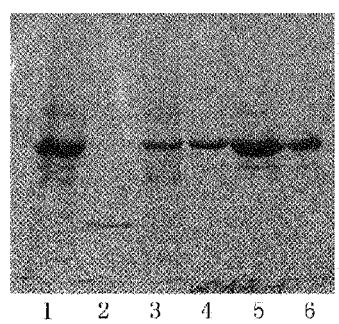
FIG. 8 is a reduced SDS-PAGE electropherogram of a chromatographically purified sample of HPV 18 L1, wherein 1 represents the collected peak 1 of POROS 50HS; 2 represents the collected peak 2 of POROS 50HS; 3 represents the collected peak 3 of POROS 50HS; 4 represents the collected peak 1 of CHT; 5 represents the concentrated sample of CHT peak 1; and 6 represents positive control.

Fine Purification:
Chromatography media CHT (BIO-RAD, Type II, 40 μm) was loaded into a chromatography column (diameter 26 mm, height 10 cm, volume 50 mL). Fine purification was conducted in the following steps: (1) washing and disinfection: the column was washed with two column volumes of 0.5 M NaOH; (2) regeneration and equilibration: the column was washed with two column volumes of Buffer H and then equilibrated with Buffer G; (3) loading sample: the sample collected after preliminary purification was added with PB to a final concentration of 30 mM and then loaded onto the column; and (4) rinsing: the column was rinsed with five column volumes of Buffer G until the baseline stabilized; (5) elution: the column was eluted with a linear gradient of 100% Buffer G to 100% Buffer H; and (6) collection: the elution fractions were collected and the fractions containing truncated HPV 18L1 protein were combined to obtain the final purified sample. The purified sample was reduced to monomeric proteins which were then subjected to reduced SDS-PAGE (Bio-RAD), demonstrating a purity of greater than 90% (see FIG. 8).

Figure 9:
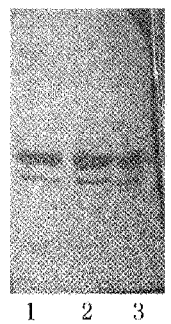
FIG. 9 shows the immunoblotting of the purified product of HPV 18 L1, wherein the primary antibody is anti-HPV-18 L1 antibody available from Fitzgerald Corp. at 1:5000 dilution; the secondary antibody is goat anti-mouse antibody at 1:250 dilution; 1 represents positive control; and both 2 and 3 represent purified HPV 18 L1 protein.
Figure 10:
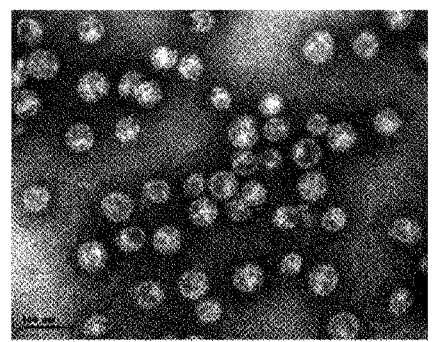
FIG. 10 is a transmission electron micrograph (×105000) of the purified sample of HPV 18 L1 VLPs.

Western blot (Bio-RAD) detection showed specific staining reaction between target electrophoresis band and monoclonal or polyclonal antibody to HPV 18 L1 protein (see FIG. 9). Dynamic light scattering detection (Malvern Instruments Zetasizer Nano ZS) showed that the purified sample had particles in a size range of about 50 to 80 nm, and electron microscopy observation (Philips Tecnai-12Biotwin transmission electron microscope, Electron Microscope Laboratory, Science and Technology Center, Shanghai University of Traditional Chinese Medicine, China) revealed virus-like particles (VLPs) in the purified sample, with the particle size in the range of about 50 to 80 nm (see FIG. 10). The full-length HPV 18L1 protein expressed as described hereinabove, when purified in the same manner, also afforded purified VLPs which were revealed by dynamic light scattering and electron microscopy detection to have the same particle size as truncated HPV 18L1 protein particles, ranging from 50 to 80 nm.

EXAMPLE 12

Preparation of Truncated HPV 18L1 Vaccine

The purified HPV 18L1 protein obtained in Example 11 above was adsorbed to an aluminium adjuvant to prepare an immunogenic HPV 18L1 vaccine according to the method described in *Chinese Pharmacopoeia* (2005 edition).

EXAMPLE 13

Determination of Immunogenicity of the Expression Product of Truncated HPV 18L1 Gene Twenty-four 6 to 8 weeks old SPF BALB/c mice were divided into 4 groups, with 6 mice in each group. Mice in the first group (as the negative control group) were immunized by hypodermic injection of 0.1 mL of aluminium adjuvant-containing buffer (0.32 M sodium chloride, 0.35 mM sodium borate, 0.01% Tween-80, 0.01 M histidine, pH 6.5) for three times on days 0, 7 and 21 respectively, and mice in the other three groups (as the test groups) were similarly immunized with 0.1 mL of aluminium adjuvant-adsorbed VLPs at a concentration of 5 μg/mL, 0.5 μg/mL and 0.05 μg/mL respectively. Blood samples were collected two weeks after the third immunization. The blood samples collected were stood at 37° C. for 2 hours and then centrifuged at 4,000 g for 10 minutes. The supernatant, which was obtained as mouse polyclonal antiserum, was aspirated and stored at −20° C. Additionally, the supernatant was assayed for seroconversion rate and titer, as detailed below.

13.1. Detection of Seroconversion Rate
The purified truncated HPV 18L1 VLPs expressed by *Pichia* yeast were diluted with coating solution to 1 μg/mL. An aliquot of 0.1 mL of the dilution was added into each well of an ELISA plate, and the plate was incubated at 4° C.

overnight. The coating solution was removed from each well, which was then washed with 0.3 mL of PBST. Then, each well was blocked by incubating with 0.3 mL of blocking solution (5% skimmed milk powder+PBST) at 37° C. for 2 hours. Each well was added with 0.1 mL of test serum (sera obtained from mice immunized with aluminium adjuvant-adsorbed HPV 18L1 protein and serum obtained from mice immunized with aluminium adjuvant alone) solution obtained by diluting the serum with dilution buffer (2% skimmed milk powder+PBST) in a ratio of 1:400, and then incubated at 37° C. for 1 hour. Then the test serum solution was removed and each well was washed with 0.3 mL of washing buffer. Subsequently, each well was added with 0.1 mL of HRP labeled goat anti-mouse IgG obtained by diluting the IgG with dilution buffer in a ratio of 1:5,000 and incubated at 37° C. for 0.5 hour. Then the ELISA solution was removed and each well was washed with 0.3 mL of washing buffer. Then, each well was added with 0.1 mL DAB color development solution and allowed to react in dark at room temperature for 20 minutes. After reaction, 0.05 mL of 2 M $H_2SO_4$ stop solution was added to each well to stop the reaction, and $OD_{450}$ value was determined using an ELISA reader, with the readings shown in Table 6 below.

TABLE 6

| | $OD_{450}$ readings | | | | | |
|---|---|---|---|---|---|---|
| | Mouse 1 | Mouse 2 | Mouse 3 | Mouse 4 | Mouse 5 | Mouse 6 |
| 5 µg immunization group | 0.964 | 0.990 | 0.901 | 0.820 | 1.040 | 1.193 |
| 0.5 µg immunization group | 0.769 | 0.898 | 0.830 | 1.706 | 0.763 | 0.982 |
| 0.05 µg immunization group | 0.933 | 0.953 | 1.422 | 1.502 | 0.572 | 1.489 |
| Aluminium adjuvant group | 0.097 | 0.146 | 0.114 | 0.176 | 0.110 | 0.158 |
| Cutoff value | 0.226 | | | | | |

The Cutoff value is the sum of the average of the $OD_{450}$ values of antibody to test serum of negative control (mouse serum obtained from immunization with aluminium adjuvant) plus three times the standard deviation. Mouse with an $OD_{450}$ value greater than the Cutoff value was regarded as positive, and mouse with an $OD_{450}$ value lower than the Cutoff value was regarded as negative. The results of seroconversion rate for the three test groups are shown in Table 7 below.

TABLE 7

| | Results of seroconversion rate | | |
|---|---|---|---|
| | 5 µg/mL immunization group | 0.5 µg/mL immunization group | 0.05 µg/mL immunization group |
| Seroconversion rate | 100% | 100% | 100% |

13.2. Determination of Serum Titer

The purified truncated HPV 18L1 protein was diluted with coating solution to 1 µg/mL. An aliquot of 0.1 mL of the dilution was added into each well of an ELISA plate, and the plate was incubated at 4° C. overnight. The coating solution was removed from each well, which was then washed with 0.3 mL of PBST. Then, each well was blocked by incubating with 0.3 mL of blocking solution (5% skimmed milk powder+PBST) at 37° C. for 2 hours. The test sera (sera obtained from mice immunized with HPV 18L1 protein) was serially double diluted with dilution buffer (2% skimmed milk powder+PBST) from 1:500 dilution to 1:32,000 dilution, while the negative control serum (serum obtained from mice immunized with aluminium adjuvant) was diluted in a ratio of 1:10,000. Each well was added with an aliquot of 0.1 mL of diluted serum (test serum or negative control serum) and incubated at 37° C. for 1 hour. Then the test serum solution was removed and each well was washed with 0.3 mL of washing buffer. Subsequently, each well was added with 0.1 mL of HRP labeled goat anti-mouse IgG obtained by diluting the IgG with dilution buffer in a ratio of 1:5,000, and incubated at 37° C. for 0.5 hour. Then the ELISA solution was removed and each well was washed with 0.3 mL of washing buffer. Then, each well was added with 0.1 mL DAB color development solution and allowed to react at room temperature for 20 minutes. After reaction, 0.05 mL of 2 M $H_2SO_4$ stop solution was added to each well to stop the reaction, and $OD_{450}$ value was determined using an ELISA reader. Serum titers were calculated by end point titration method, with the results shown in Table 8 below.

TABLE 8

| | Results of titer determination | | | | | |
|---|---|---|---|---|---|---|
| | Mouse 1 | Mouse 2 | Mouse 3 | Mouse 4 | Mouse 5 | Mouse 6 |
| 5 µg immunization group | 418416 | 83602 | 252997 | 192334 | 470324 | 215223 |
| 0.5 µg immunization group | 1073694 | 13854 | 189584 | 18371 | 226400 | 192297 |
| 0.05 µg immunization group | 79083 | 68971 | 61310 | 11819 | 2000 | 14099 |

In summary, as shown in Examples 1-13, the gene for major capsid protein L1 of human papilloma virus subtype 18 or the gene for truncated major capsid protein L1 of human papilloma virus subtype 18, as provided by the present invention, is an optimized L1 gene, which has the advantages of being more suitable for efficiently expressing target protein in yeast host and meeting the requirements of industrial production. Moreover, the HPV 18L1 vaccine as provided by the present invention can be self-assembled into the structure of VLPs. The vaccine was demonstrated to be strongly immunogenic in mice as determined by seroconversion rate and serum titer with the adjuvant-adsorbed purified VLPs. Further, the method has the advantages of low cost, high yield, and more uniform and stable quality of products due to the use of *Pichia* yeast expression system.

EXAMPLE 14

Neutralization Activity of Truncated HPV 18 L1 VLPs

Mice were immunized with the same procedure as described above and blood was collected two weeks after immunization. The collected blood was stood at 37° C. for 2 hours, then centrifuged at 4,000 g for 10 minutes. The supernatant, which was obtained as mouse polyclonal antiserum, was aspirated and stored at −20° C.

293FT cells (Invitrogen) were initially plated onto 15 cm cell culture dish ($1.1 \times 10^7$ cells/dish). Twenty-four hours later, the cells were cotransfected with plasmids p18L1 h, p18L2 h (Buck C B, Pastrana D V, Lowy D R et al. Efficient Intracellular Assembly of Papillomaviral Vectors. J Virol, 2004, 78(2):751-757) and green fluorescent gene-carrying pIRES2-EGFP (purchased from BD Biosciences Clontech) respectively in an amount of 20 μg, 10 μg and 10 μg using calcium phosphate transfection method. Forty-eight hours later, cells were observed, collected and lysed. Cell lysis supernatant was immediately subjected to purification or stored at −80° C.

Purification was performed by centrifuging the cell lysis supernatant in a 5 mL centrifugation tube (Beckman) using 30% OptiPrep density gradient centrifugation at 100,000 g at 16° C. for 4 hours (MLS-50 centrifuge rotor, Beckman ultraspeed centrifuge). The centrifugation fractions were collected, each fraction being about 500 μL, and assayed for the content of HPV 18 L1 protein using Western blotting. The fractions having highest concentration of L1 protein were combined as pseudotype virus solution, which was then aliquoted and stored at −80° C.

Figure 11A:
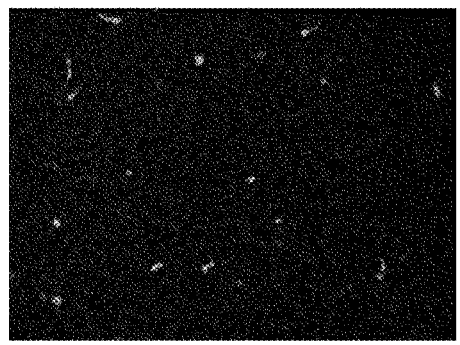
FIG. 11A is a diagram depicting infection of 293FT cell by HPV 18 pseudotype virus.
Figure 11B:
FIG. 11B is a diagram depicting neutralization of HPV 18 pseudotype virus by murine serum.

293FT cells were plated onto 24-well cell culture plate ($1.5 \times 10^5$ cells/well). Twenty-four hours later, neutralization experiment was done as follows. Different serum samples were serially diluted 100-fold with DMEM medium. An aliquot of 50 μL of each dilution was mixed with 50 μL of the pseudotype virus solution diluted in DMEM medium, and each mixture was incubated at 4° C. for 1 hour. Then each incubated mixture was added into the 24-well cell culture plate pre-plated with 293FT cells and incubated at 37° C. for 48 hours. After incubation, the cells were observed for expression of green fluorescent protein under an OLUMPUSCKX41F32FL inverted fluorescence microscope, and fluorescence images were collected, as shown in FIGS. 11a and 11b. Fluorescence was seen in FIG. 11a, which indicates that the HPV 18 pseudotype virus had infected the 293FT cells. Little fluorescence remained in FIG. 11b, which indicates that mouse serum had neutralized the HPV 18 pseudotype virus, thereby reducing the viral infection of the 293FT cells. It is therefore clear that mice immunized with recombinant HPV 18L1 VLPs vaccine could generate neutralizing antibody which would inhibit entry of the pseudotype virus into cells.

In the present invention, nucleotide sequence SEQ ID NO: 2 or 3 and nucleotide sequence SEQ ID NO: 5 or 6 can respectively be substituted for SEQ ID NO: 1 and SEQ ID NO: 4 in the above examples to prepare HPV 18 L1 protein and truncated form thereof of the present invention using the methods as described in the above examples. In addition, the above-said genes can also be cloned, in appropriate cloning manner, into other existing Pichia yeast expression vector, such as pPIC6, pGAPZ or pAO815. Then the recombinant expression vectors obtained can be used to transform other Pichia yeast strains, such as Pichia pastoris GS115, KM71 or SMD1168 strains, so as to construct genetically engineered strains. Using conventional methods of culturing and fermentation, and separation and purification (which are not detailed herein), HPV 18 L1 protein (HPV 18 L1 VLPs) or truncated form thereof of the present invention can be obtained from the genetically engineered strains. Thus prepared HPV 18 L1 protein or truncated form thereof will have similar immunogenicity to that of the HPV 18 L1 protein or truncated form thereof prepared in the above examples.

EXAMPLE 15

Design and Synthesis of Codon-Optimized Gene for HPV 16 L1

15.1. Design of Codon-Optimized Gene for HPV 16 L1

The present invention relates to DNA molecules encoding the major capsid protein L1 of human papilloma virus subtype 16 (HPV16), which have been codon-optimized with codons preferred by Pichia yeast. Three DNA sequences, which are as set forth in SEQ ID NO: 7, 8 and 9, respectively, were obtained through optimization of codons and alteration of optimized codons, as detailed below.

Firstly, through repeated experiments, modifications were made on the naturally-occurring gene encoding HPV 16L1 by optimizing the codons for all the corresponding amino acids of the gene to design a novel HPV DNA sequence, that is, SEQ ID NO:7.

Then, in order to avoid the presence of a high GC ratio in the transcribed mRNAs, the influence of mRNA secondary structure on the efficiency of translation, and the occurrence of common restriction sites, alterations were made to the optimized codons, such as, the codon for asparagine (Asn) being altered from AAC to AAT, the codon for lysine (Lys) being altered from AAG to AAA, the codon for aspartic acid (Asp) being altered from GAT to GAC, the codon for phenylalanine (Phe) being altered from TTT to TTC, the codon for tyrosine (Tyr) being altered from TAC to TAT, and the codon for glycine (Gly) being altered from GGT to GGA, thus obtaining two novel HPV DNA sequences, wherein:

SEQ ID NO: 8 is the DNA sequence obtained from SEQ ID NO: 7 by altering the codons for asparagine (Asn), lysine (Lys) and aspartic acid (Asp); SEQ ID NO: 9 is the DNA sequence obtained from SEQ ID NO: 7 by altering the codons for phenylalanine (Phe), tyrosine (Tyr) and glycine (Gly).

15.2. Synthesis of Codon-Optimized Gene for HPV 16 L1

The codon-optimized gene for HPV 16 L1 as set forth in SEQ ID NO: 7 was synthesized and used as template to perform PCR amplification using primers a1 and a2 which have the following sequences:

```
                                         (SEQ ID NO: 16)
    a1:   5'-ATAGAATTCATGTCTTTGTGGTTGCCATC-3';

(SEQ ID NO: 17)
    a2:   5'-ATAGGTACCCTATTACAACTTTCTCTTCTTT-3'.
```

The PCR products obtained were subjected to separation by agarose gel electrophoresis and the target sequence was recovered from the gel, obtaining a fragment about 1.5 kb in size. This fragment was sequenced, with the result of sequencing as shown in SEQ ID NO: 7, and was demonstrated from the result to be the full-length codon-optimized gene for HPV 16L1. Thus obtained gene for HPV 16L1, by virtue of the EcoRI and KpnI restriction sites on its ends, was ligated into pUC18 plasmid (available from Generay Biotech (Shanghai) Co., Ltd (Shanghai, China)). The resulting construct was verified by sequencing to be correct, and was named as pUC-16L1.

Codon-optimized genes for HPV 16L1 as shown in SEQ ID NO: 8 and 9 were obtained in a similar procedure as above.

In order to verify the feasibility of the optimized sequences, one of the codon-optimized genes for HPV 16L1 obtained in this Example 15 (SEQ ID NO: 7) was exemplarily used to construct an expression plasmid to assess for its expression as follows.

EXAMPLE 16

Construction of Expression Vector of HPV 16L1 Gene

Figure 12:
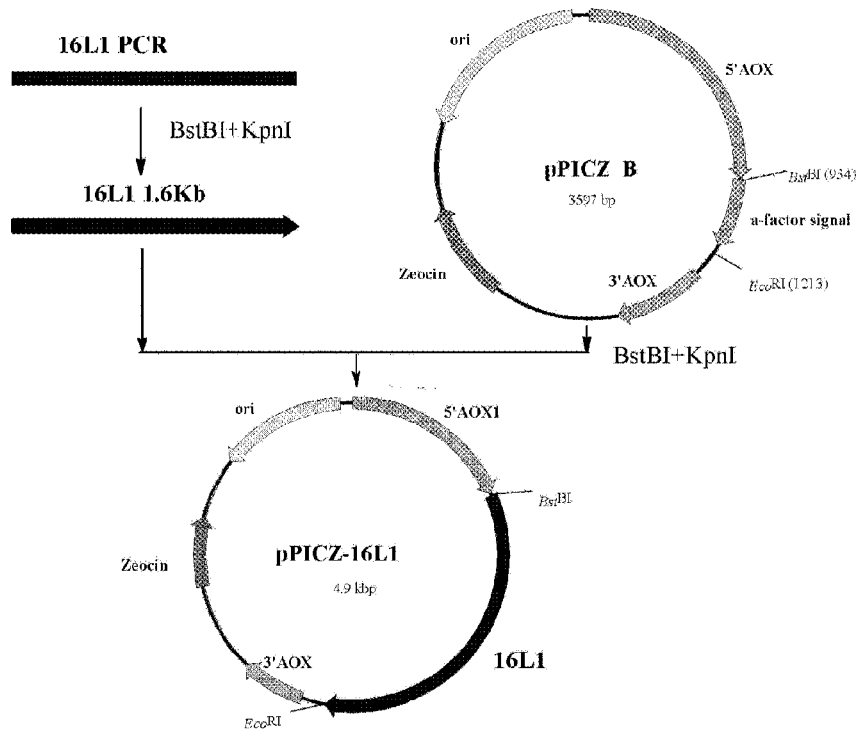
FIG. 12 is a schematic depiction of the construction of pPICZ-16 L1 vector.

The optimized sequence of SEQ ID NO: 7 was cloned into *Pichia* yeast expression vector as shown in FIG. 12 and as detailed in the following steps.

16.1. The forward and reverse primers having the following sequences, which were required for amplifying HPV 16L1 gene, were synthesized:

```
forward primer:
                                   (SEQ ID NO: 18)
5'-ACTAATTATTCGAAACGATGTCTTTGTGG-3';

reverse primer:
                                   (SEQ ID NO: 19)
5'-AGCGGTACCCTATTACAACTTTCTCTTCTTTC-3'.
```

Wherein the forward primer comprises a BstBI restriction site, and the reverse primer comprises a KpnI restriction site flanking the termination codon, said restriction sites respectively as shown in the underlined portions of the primer sequences above.

16.2. PCR amplification was performed using the above primers and using the pUC-16L1 obtained in Example 15 as template. The amplified product was detected by electrophoresis, with the result being shown in FIG. 13, demonstrating that a full-length codon-optimized gene for HPV 16L1 was obtained. The PCR amplified fragment was digested with BstBI and KpnI (restriction endonucleases) and then ligated with pPICZaB (Invitrogen Corp.) which was also digested with BstBI and KpnI. Then, the ligated construct was used to transform competent cells of *E. coli* Top10 strain (available from Generay Biotech (Shanghai) Co., Ltd (Shanghai, China)), and the transformed cells were plated onto LB agar containing 25 µg/ml of zeocin.

The transformed cells were able to grow on LB media containing zeocin as the pPICZaB vector carried zeocin-resistance gene. Single colonies of the transformed cells were separated to prepare plasmid DNA. HPV 16L1 gene and vector sequence were detected through restriction mapping (see FIG. 14) and nucleotide sequence analysis to identify the correct construct comprising HPV 16L1 gene, which was named pPICZ-16L1. As secretion signal (a-factor signal) has been cleaved from the constructed plasmid, therefore the HPV 16L1 protein expressed should be intracellularly expressed protein.

EXAMPLE 17

Construction and Expression of HPV 16L1 Gene-Expressing *Pichia* Yeast Strain 17.1. Construction of HPV 16L1 Gene-Expressing *Pichia* Yeast Strain pPICZ-16L1 plasmid was linearized with a restriction endonuclease enzyme SacI, and empty plasmid pPICZaB was likewise digested with SacI to serve as negative control. The enzyme digestion solution was added with absolute ethanol to obtain DNA precipitate. The linearized pPICZ-16L1 fragment was dissolved with a small amount of double-distilled water and used to transform *Pichia* yeast strain X-33 (Invitrogen Corp.) by electroporation under the following conditions: DNA fragment, 5 µg; voltage, 1,500 volts; resistance, 25 omhs; electroporation time, 5 milliseconds. The electroporated cells were plated onto YPDS agar containing 200 µg/ml zeocin (from Zeocin). As the pPICZaB vector carried zeocin-resistance gene, the transformed cells were able to grow on YPDS media containing zeocin. Single colonies of transformed cells were isolated, thus obtaining HPV 16L1 gene-expressing *Pichia* yeast strain.

17.2. Expression of HPV 16L1 Gene-Expressing *Pichia* Yeast Strain

Figures 13, 14, 15:
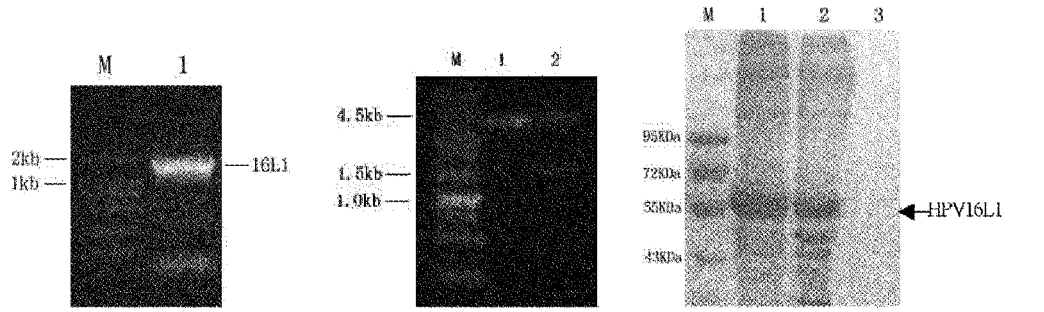
FIG. 13 is a diagram of PCR amplification of the gene for HPV 16 L1.
FIG. 14 is a diagram of identification of pPICZ-16 L1 vector, wherein lane 1 represents BstBI- and KpnI-digested pPICZαB; and lane 2 represents BstBI- and KpnI-digested pPICZ-16L1.
FIG. 15 is a diagram of Western blot identification of the expression of HPV 16 L1, wherein M represents Rainbow Marker (Fermentas Co., Ltd); 1 represents the positive control of expression; 2 represents the strain expressing HPV 16 L1; and 3 represents the negative control of expression. The arrow designates the expressed HPV 16 L1.

The obtained HPV 16L1 gene-expressing *Pichia* yeast strain was plated onto resistance plates containing 1,000 µg/ml or 1,500 µg/ml zeocin. Clones obtained from plates having high concentration of resistance were separately cultured in 4 mL of YPD liquid culture media for 24 hours followed by induction of gene expression in BMMY culture media for 48 hours. Then cells were harvested by centrifugation and some of the cells were disrupted to obtain supernatant for performing Western blotting identification. The result of identification is shown in FIG. 15, which indicated the presence of HPV 16L1 protein in the supernatant.

Although SEQ ID NO: 7 sequence was used for cloning and expression in Examples 16 and 17 of the present invention, it will be obvious to those skilled in the art that similar results can be obtained when SEQ ID NO: 8 and 9 sequences are used for cloning and expression, and therefore these two sequences are also within the scope of the present invention. Moreover, those skilled in the art will, in light of the spirit of the present invention, readily construct similar sequences and clone and express the constructed sequences in *Pichia* yeast to obtain similar or better results, and therefore these sequences are also deemed to be within the scope of the present invention.

EXAMPLE 18

Large-Scale Expression and Detection of HPV 16L1 Protein

1. Large-Scale Expression of Recombinant HPV 16L1 Protein

Preparation of inoculum solution: One glycerol freezing tube of recombinant yeast stock was taken from working cell bank. After thawing, 100 µL of the stock was inoculated into 5 mL of YPD media and cultured at 280 rpm at 30° C. for 20 hours, at which time $OD_{600}$ was detected to be 1 to 2 and no contamination from other microorganisms was microscopically observed. 1 mL of the activation fluid (which has been inspected to be satisfactory) was inoculated into 500 mL of YPD media and cultured at 280 rpm at 30° C. for 20 hours, at which time $OD_{600}$ was detected to be 2 to 6 and no contamination from other microorganisms was microscopically observed.

Process of fermentation: Basal salt medium for fermentation was prepared using deionized water: $BSM_1$($K_2SO_4$ 273 g, $MgSO_4$ 109 g, $CaSO_4.2H_2O$ 17.6 g, $H_3PO_4$ 400.5 mL, KOH 62 g, glycerol 600 g, $PTM_1$ 60 mL, defoamer 1 mL; add deionized water to a volume of 15 L). The prepared medium, which contained no antibiotics, was transferred into a 30 L fermentation tank (Bioengineering Co., Ltd) and sterilized in the tank at 121° C. for 30 minutes, followed by cooling to 30° C. The inoculum solution previously prepared was used to inoculate the sterilized medium in a ratio of 1:15. Fermentation was started at a temperature of 30.0±0.5° C., an initial pH of 5.00±0.05, an initial stirring speed of 300 rpm, an aeration volume of 0.5 vvm and a dissolved oxygen (DO) of 100%, with addition of trace salts $PTM_1$ ($CuSO_4 \cdot 5H_2O$ 6.0 g, NaI 0.008 g, $MnSO_4$ 3.0 g, $NaMoO_4$ 0.2 g, $H_3BO_3$ 0.02 g, $ZnSO_4$ 20.0 g, $CoCl_2$ 0.5 g, $FeSO_4 \cdot 7H_2O$ 65.0 g, biotin 0.2 g, and $H_2SO_4$ 5.0 mL; add deionized water to a volume of 1 L). The initial proliferation stage lasted for about 20 hours, during which time the dissolved oxygen was maintained at no lower than 30%. When the carbon source was completely consumed, the dissolved oxygen increased rapidly, at which time the wet cell weight was up to about 100 g/L. In the subsequent two hours, the fermentation was supplemented with 50% (v/v) glycerol solution (added with 12 mL of $PTM_1$ per liter) at a rate of 200 mL/h. Then the supplementation was continued at a rate of 300 mL/h for about 8 hours, during which time the dissolved oxygen was maintained at higher than 20% by adjusting the stirring speed, air flow and tank pressure (<0.8 bar). When the wet cell weight reached about 350 g/L, supplementation was stopped, and the dissolved oxygen increased accordingly. Meanwhile, the pH value was adjusted to 6.00±0.05, and methanol (added with 12 mL of $PTM_1$ per liter) was added at an initial addition rate of 30 mL/h to induce gene expression. The addition rate of methanol was increased slowly until a set rate of 90 mL/h after 4 hours. During induction, the dissolved oxygen was maintained at higher than 20% (v/v), the temperature at 30° C. and the pH at 6.00±0.05. Sample was taken every eight hours and subjected to Western blotting detection. Twenty-four hours after induction, the fermentation completed and the fermentation broth was discharged.

Harvest of cells: The fermentation broth was centrifuged using a refrigerated centrifuge to collect the cells, which were then weighed. The batch number, date and weight for the recovered cells were recorded, and the cells were sent for purification or stored at −20° C.

2. Detection

The purified (according to the method described in Example 19 below) HPV 16L1 protein was used to prepare a protein concentration standard curve. With cells before induction as negative control, the expression amount of HPV 16L1 gene in *Pichia* yeast during fermentation was detected using sandwich ELISA method, as detailed below.

Rabbit polyclonal antibody to HPV16L1 protein was diluted 2,000 fold with coating solution. An aliquot of 0.1 mL of the diluted rabbit polyclonal antibody was added to each well of an ELISA plate, and the plate was incubated at 4° C. overnight. The coating solution was removed from each well, which was then washed with 0.3 mL of PBST. Then, each well was blocked by incubating with 0.3 mL of blocking solution at 37° C. for 2 hours.

The purified HPV 16L1 protein was gradiently diluted with dilution buffer from a concentration of 2 µg/mL to 0.0625 µg/mL. Meanwhile, the supernatant obtained from disrupted fermentation broth was diluted 200 fold. Then, for each of the HPV 16 L1 protein solutions of different concentrations obtained by the serial dilution and for the diluted supernatant, an aliquot of 0.1 mL was taken and added to a separate well of the ELISA plate, and the plate was incubated at 37° C. for 1 hour. After incubation, the aliquot of antigen solution was removed from each well, which was then washed with 0.3 mL of washing buffer. Then, MAB885 mouse monoclonal antibody (purchased from CHEMICON Co., Ltd) was diluted 1,000 fold with dilution buffer, and an aliquot of 0.1 mL of the dilution was added to each well and incubated at 37° C. for 1 hour. Following incubation, the monoclonal antibody solution was removed from each well, which was then washed with 0.3 mL of washing buffer. Subsequently, each well was added with 0.1 mL of HRP labeled goat anti-mouse IgG obtained by diluting the IgG 5,000-fold with dilution buffer, and incubated at 37° C. for 0.5 hour. Then the ELISA solution was removed and each well was washed with 0.3 mL of washing buffer. Then, each well was added with 0.1 mL DAB color development solution, and interaction was allowed to occur at room temperature for 20 minutes. Afterwards, 0.05 mL of 2 M $H_2SO_4$ stop solution was added to each well to stop the reaction, and $OD_{450}$ value was determined using an ELISA reader.

The $OD_{450}$ values for the gradiently diluted solutions of HPV 16L1 protein were used to prepare a protein concentration standard curve. Using this standard curve, the expression amount of HPV 16L1 protein during fermentation was obtained, as shown in Table 9 below. Particularly speaking, the purified target protein stock solution with known concentration was serially diluted into solutions of a range of concentrations, such as 2 µg/mL, 1 µg/mL, 0.5 µg/mL, 0.25 µg/mL and 0.125 µg/mL, which were used as standard concentrations. ELISA detection was conducted on these solutions to obtain the corresponding $OD_{450}$ values. Then a standard linear regression equation was generated, with the ordinate representing the concentration and the abscissa representing the $OD_{450}$ value.

The supernatant obtained from the disrupted fermentation broth was serially diluted, such as being diluted 50 fold, 100 fold, 200 fold and 400 fold. $OD_{450}$ values were detected for these serial dilutions, and the corresponding concentrations (µg/mL) were found from the standard linear regression equation. The concentration of the target protein in the supernatant (µg/mL) was then calculated by multiplying the found concentration with the corresponding dilution factor. As the disrupted broth was prepared from wet cell weight:cell disruption buffer=1:5, therefore the expression amount of the target protein in the wet cells (µg/g wet cells) was 5× the concentration of the target protein in the supernatant (µg/mL). And the concentration of expression of the target protein in the fermentation broth (µg/L fermentation broth) was obtained by multiplying the above-obtained expression amount of the target protein in the wet cells with the density of cells in the fermentation broth (g wet cells/L fermentation broth).

Concentration of the target protein in the supernatant obtained from the disrupted fermentation broth (µg/mL)=Dilution factor×Concentration of standard target protein (µg/mL)×$OD_{450}$ (supernatant obtained from the disrupted fermentation broth)/$OD_{450}$ (standard target protein concentration);

Concentration of expression of the target protein in the fermentation broth (µg/L fermentation broth)=5×Concentration of the target protein in the supernatant obtained from the disrupted fermentation broth (µg/mL)×Density of cells in the fermentation broth (g wet cells/L fermentation broth).

TABLE 9

Detection of expression of HPV 16L1 protein during fermentation

| Sample | Dilution factor | $OD_{450}$ | Concentration of stock solution (μg/mL) | Average concentration (μg/mL) | Converted concentration | Fermentation density | Expression amount during fermentation |
|---|---|---|---|---|---|---|---|
| Disrupted fermentation broth | 200 | 0.601 | 382 | 381 | 1904 μg/g wet cells | 472 g/L | 899 mg/L fermentation broth |
| Supernatant 1 | 100 | 1.034 | 379.5 | | | | |
| Disrupted fermentation broth | 200 | 0.826 | 578.1 | 542 | 2708 μg/g wet cells | 347 g/L | 940 mg/L fermentation broth |
| Supernatant 2 | 100 | 1.323 | 505.1 | | | | |
| Negative control | 100 | 0.085 | | | | | |
| Blank control | — | 0.077 | | | | | |

It can be seen from the results shown in Table 9 that, the optimized sequence of the gene for HPV 16L1 protein according to the present invention not only can be expressed into HPV 16L1 protein in *Pichia* yeast, but also has a high expression amount, meeting the requirements of industrial production.

EXAMPLE 19

Purification of HPV 16L1 Protein

Cleaning:

The above-obtained *Pichia* yeast cells expressing HPV 16 L1 protein, which had been stored at −20° C., was thawed at room temperature. Then the thawed cells were mixed with washing buffer (100 mM PB, pH 7.0, 0.15 M NaCl) or water for purification in a ratio of 1:3 (g/mL), and completely homogenized with the buffer or water in a homogenizer (FLUKO). Subsequently, the homogenate was subjected to high speed centrifugation (SORVALLRC6PLUS) at 8000 rpm for 5 minutes to separate the cells, the supernatant being decanted. The above procedure was repeated twice, thereby achieving the cleaning of the cells.

Disruption:

The cleaned cells were added and mixed into cell disruption buffer (200 mM MOPS, pH 7.0, 0.4 M NaCl, 0.05% Tween-80) in a ratio of 1:5 (g/mL), and completely homogenized with the buffer in a homogenizer (FLUKO). The cells suspended in the homogenate were subjected to disruption using a high-pressure homogenizer (ATSAH110B) operating at a pressure in the range of 1200 to 1300 bars. This disruption was repeated four times, and then the disrupted cell solution was discharged at 4 to 8° C., with 90% of the cells being disrupted.

Clarification:

The disrupted cell solution obtained by high-pressure disruption as above was poured into a centrifugation cup and centrifuged at high speed to precipitate cell debris, obtaining supernatant for subsequent column chromatography separation. The centrifuge used is SORVALLRC6PLUS, rotor model: FIBERLITEF10-6x500y, centrifugation setting: 9,000 rpm, 30 min, 10° C.

Preliminary Purification:

Chromatography media POROS 50HS (Applied Biosystems) was loaded into a chromatography column (diameter 26 mm, height 10 cm, volume 50 mL). Preliminary purification was conducted in the following steps: (1) washing and disinfection: the column was washed with two column volumes of 0.5 M NaOH; (2) regeneration and equilibration: the column was washed with two column volumes of Buffer F and then equilibrated with Buffer E; (3) loading sample: the supernatant obtained by centrifuging the disrupted cell solution as above was loaded onto the column; (4) rinsing: the column was rinsed with five column volumes of Buffer E until the baseline stabilized; (5) elution: the column was eluted with a linear gradient of 100% Buffer E to 100% Buffer F; and (6) collection: the elution fractions were collected, and the fractions containing HPV 16 L1 protein (detected by SDS-PAGE and Western blotting) were combined and used for fine purification.

Figure 16:
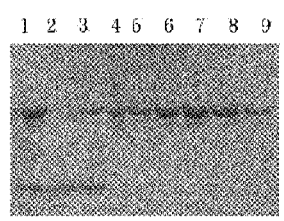
FIG. 16 is a reduced SDS-PAGE electropherogram of a chromatographically purified sample of HPV 16 L1, wherein 1 represents the collected peak sample of POROS 50HS; 2 represents CHT flowthrough 1; 3 represents CHT flowthrough 2; 4 represents HPV 16 L1 positive control; 5 represents CHT elution peak 1; 6 represents CHT elution peak 2; 7 represents CHT elution peak 4; 8 represents CHT elution peak 8; and 9 represents CHT elution peak 12.
Figure 17:
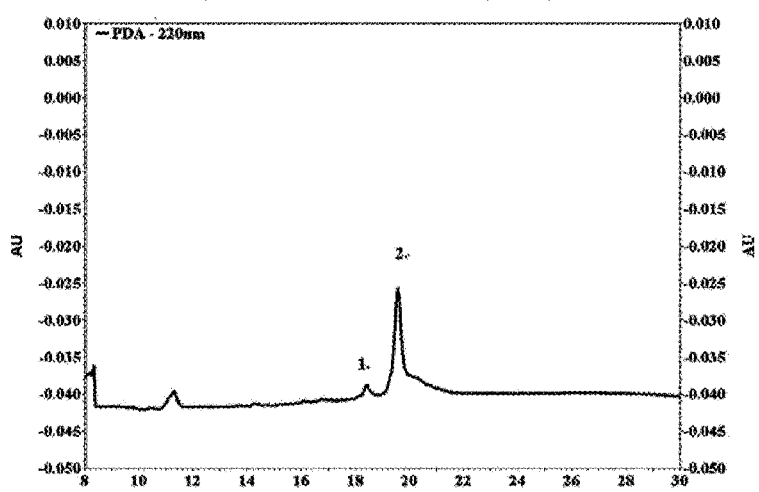
FIG. 17 shows the purity of HPV 16 L1 as determined by capillary electrophoresis.

Fine Purification:

Chromatography media CHT (BIO-RAD, Type II, 40 μm) was loaded into a chromatography column (diameter 26 mm, height 10 cm, volume 50 mL). Fine purification was conducted in the following steps: (1) washing and disinfection: the column was washed with two column volumes of 0.5 M NaOH; (2) regeneration and equilibration: the column was washed with two column volumes of Buffer H and then equilibrated with Buffer G; (3) loading sample: the sample collected after preliminary purification was added with PB to a final concentration of 20 mM and then loaded onto the column; and (4) rinsing: the column was rinsed with five column volumes of Buffer G until the baseline stabilized; (5) elution: the column was eluted with a linear gradient of 100% Buffer G to 100% Buffer H; and (6) collection: the elution fractions were collected and the fractions containing HPV 16L1 protein were combined to obtain the final purified sample. The purified sample was reduced to monomeric proteins which were then subjected to reduced SDS-PAGE (Bio-RAD) (see FIG. 16) and capillary electrophoresis (see. FIG. 17), demonstrating a purity of greater than 90%. The parameters of capillary electrophoresis for HPV 16L1 is as following:

| | Results of detection at 220 nm wavelength | | | |
|---|---|---|---|---|
| Peak | Retention time | Peak height | Peak area after calibration | Proportion of peak area after calibration |
| 1 | 18.417 | 1530 | 1175.79185520 | 6.30041539 |
| 2 | 19.583 | 14269 | 17486.34042553 | 93.69958461 |
| Total | | 15799 | 18662.13228074 | 100.00000000 |

Figure 18:
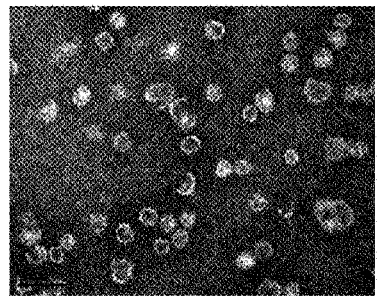
FIG. 18 is a transmission electron micrograph (×105000) of the purified sample of HPV 16 L1 VLPs.

Western blot (Bio-RAD) detection showed specific staining reaction between target electrophoresis band and monoclonal or polyclonal antibody to HPV 16 L1 protein. Dynamic light scattering detection (Malvern Instruments Zetasizer Nano ZS) showed that the purified sample had particles in a size range of about 50 to 80 nm, and electron microscopy observation (Philips Tecnai-12Biotwin transmission electron microscope, Electron Microscope Laboratory, Science and Technology Center, Shanghai University of Traditional Chinese Medicine, China) revealed the structure of virus-like particles (VLPs) in the purified sample, with the particle size in the range of about 50 to 80 nm (see FIG. 18).

EXAMPLE 20

Preparation of HPV 16L1 Vaccine

The purified HPV 16L1 protein obtained in Example 19 above was adsorbed to an aluminium adjuvant to prepare an immunogenic HPV 16L1 vaccine according to the method described in *Chinese Pharmacopoeia* (2005 edition).

EXAMPLE 21

Determination of Immunogenicity of the Expression Product of HPV 16L1 Gene

Twenty-four 6 to 8 weeks old SPF BALB/c mice were divided into 4 groups, with 6 mice in each group. Mice in the first group (as the negative control group) were immunized by hypodermic injection of 0.1 mL of aluminium adjuvant-containing buffer (0.32 M sodium chloride, 0.35 mM sodium borate, 0.01% Tween-80, 0.01 M histidine, pH 6.5) for three times on days 0, 7 and 21 respectively, and mice in the other three groups (as the test groups) were similarly immunized with 0.1 mL of aluminium adjuvant-adsorbed VLPs at a concentration of 5 μg/mL, 0.5 μg/mL and 0.05 μg/mL respectively. Blood samples were collected two weeks after the third immunization. The blood samples collected were stood at 37° C. for 2 hours and then centrifuged at 4,000 g for 10 minutes. The supernatant, which was obtained as mouse polyclonal antiserum, was aspirated and stored at −20° C. Additionally, the supernatant was assayed for seroconversion rate and titer, as detailed below.

21.1. Detection of Seroconversion Rate

The purified HPV 16L1 VLPs expressed by *Pichia* yeast were diluted with coating solution to 1 μg/mL. An aliquot of 0.1 mL of the dilution was added into each well of an ELISA plate, and the plate was incubated at 4° C. overnight. The coating solution was removed from each well, which was then washed with 0.3 mL of PBST. Then, each well was blocked by incubating with 0.3 mL of blocking solution (5% skimmed milk powder PBST) at 37° C. for 2 hours. Each well was added with 0.1 mL of test serum (serum obtained from mice immunized with aluminium adjuvant-adsorbed HPV 16L1 protein and serum obtained from mice immunized with aluminium adjuvant alone) solution obtained by diluting the serum with dilution buffer (2% skimmed milk powder+ PBST) in a ratio of 1:400, and then incubated at 37° C. for 1 hour. Then the test serum solution was removed and each well was washed with 0.3 mL of washing buffer. Subsequently, each well was added with 0.1 mL of HRP labeled goat anti-mouse IgG obtained by diluting the IgG with dilution buffer in a ratio of 1:5,000 and incubated at 37° C. for 0.5 hour. Then the ELISA solution was removed and each well was washed with 0.3 mL of washing buffer. Then, each well was added with 0.1 mL DAB color development solution and allowed to react in dark at room temperature for 20 minutes. After reaction, 0.05 mL of 2 M $H_2SO_4$ stop solution was added to each well to stop the reaction, and $OD_{450}$ value was determined using an ELISA reader, with the readings shown in Table 10 below.

TABLE 10

| | $OD_{450}$ readings | | | | | |
|---|---|---|---|---|---|---|
| | Mouse 1 | Mouse 2 | Mouse 3 | Mouse 4 | Mouse 5 | Mouse 6 |
| 5 μg immunization group | 1.306 | 1.961 | 1.840 | 1.280 | 0.992 | 0.889 |
| 0.5 μg immunization group | 0.194 | 1.526 | 0.795 | 0.220 | 0.263 | 1.056 |
| 0.05 μg immunization group | 0.786 | 1.481 | 0.648 | 0.377 | 0.287 | 0.161 |
| Aluminium adjuvant group | 0.100 | 0.137 | 0.092 | 0.119 | 0.099 | 0.128 |
| Cutoff value | 0.167 | | | | | |

The Cutoff value is the sum of the average of the $OD_{450}$ values of antibody to test serum of negative control (mouse serum obtained from immunization with aluminium adjuvant) plus three times the standard deviation. Mouse with an $OD_{450}$ value greater than the Cutoff value was regarded as positive, and mouse with an $OD_{450}$ value lower than the Cutoff value was regarded as negative. The results of seroconversion rate for the three test groups are shown in Table 11 below.

TABLE 11

| | Results of seroconversion rate | | |
|---|---|---|---|
| | 5 μg/mL immunization group | 0.5 μg/mL immunization group | 0.05 μg/mL immunization group |
| Seroconversion rate | 100% | 100% | 83% |

21.2. Determination of Serum Titer

The purified HPV 16L1 protein was diluted with coating solution to 1 μg/mL. An aliquot of 0.1 mL of the dilution was added into each well of an ELISA plate, and the plate was incubated at 4° C. overnight. The coating solution was removed from each well, which was then washed with 0.3 mL of PBST. Then, each well was blocked by incubating with 0.3 mL of blocking solution (5% skimmed milk powder+PBST) at 37° C. for 2 hours. The test serum (serum obtained from mice immunized with HPV 16L1 protein) was serially double diluted with dilution buffer (2% skimmed milk powder PBST) from 1:500 dilution to 1:32,000 dilution, while the negative control serum (serum obtained from mice immunized with aluminium adjuvant) was diluted in a ratio of 1:10,000. Each well was added with an aliquot of 0.1 mL of diluted serum (test serum or negative control serum) and incubated at 37° C. for 1 hour. Then the test serum solution was removed and each well was washed with 0.3 mL of washing buffer. Subsequently, each well was added with 0.1 mL of HRP labeled goat anti-mouse IgG obtained by diluting the IgG with dilution buffer in a ratio of 1:5,000, and incubated at 37° C. for 0.5 hour. Then the ELISA solution was removed and each well was washed with 0.3 mL of washing buffer. Then, each well was added with 0.1 mL DAB color development solution and allowed to react at room temperature for 20 minutes. After reaction, 0.05 mL of 2 M $H_2SO_4$ stop solution was added to each well to stop the reaction, and $OD_{450}$ value was determined using an ELISA reader.

Serum titers were calculated by end point titration method, with the results shown in Table 12 below.

TABLE 12

Results of titer determination

| | Mouse 1 | Mouse 2 | Mouse 3 | Mouse 4 | Mouse 5 | Mouse 6 |
|---|---|---|---|---|---|---|
| 5 μg immunization group | 71727 | 48969 | 30700 | 64289 | 118279 | 4598178 |
| 0.5 μg immunization group | 7309 | 52706 | 335668 | 4593 | 47049 | 85822 |
| 0.05 μg immunization group | 24330 | 42552 | 8421 | 5751 | 7108 | <400 |

In summary, as shown in Examples 15-21, the gene for major capsid protein L1 of human papilloma virus subtype 16, as provided by the present invention, is an optimized HPV 16L1 gene, which has the advantages of being more suitable for efficiently expressing target protein in yeast host and meeting the requirements of industrial production. Moreover, the HPV 16L1 vaccine as provided by the present invention, which was prepared from adjuvant-adsorbed purified VLPs (virus-like particles self-assembled from HPV 16L1 protein), was demonstrated to be strongly immunogenic in mice as determined by seroconversion rate and serum titer. Further, the method has the advantages of low cost, high yield and more uniform and stable quality of products can be achieved due to the use of *Pichia* yeast expression system.

EXAMPLE 22

Neutralization Activity of HPV 16 L1 VLPs

Mice were immunized in the same procedure as described above and blood was collected two weeks after immunization. The collected blood was stood at 37° C. for 2 hours, then centrifuged at 4,000 g for 10 minutes. The supernatant, which was obtained as mouse polyclonal antiserum, was aspirated and stored at −20° C.

293FT cells (Invitrogen) were initially plated onto 15 cm cell culture dish ($1.1 \times 10^7$ cells/dish). Twenty-four hours later, the cells were cotransfected with plasmids p16L1h, p16L2h (Buck C B, Pastrana D V, Lowy D R et al. Efficient Intracellular Assembly of Papillomaviral Vectors. J Virol, 2004, 78(2):751-757) and green fluorescent gene-carrying pIRES2-EGFP (purchased from BD Biosciences Clontech) respectively in an amount of 20 μg, 10 μg and 10 μg using calcium phosphate transfection method. Forty-eight hours later, cells were observed, collected and lysed. Cell lysis supernatant was immediately subjected to purification or stored at −80° C.

Purification was performed by centrifuging the cell lysis supernatant in a 5 mL centrifugation tube (Beckman) using 30% OptiPrep density gradient centrifugation at 100,000 g at 16° C. for 4 hours (MLS-50 centrifuge head, Beckman ultraspeed centrifuge). The centrifugation fractions were collected, each fraction being about 500 μL, and assayed for the content of HPV 16 L1 protein using Western blotting. The fractions having highest concentration of L1 protein were combined as pseudotype virus solution, which was then aliquoted and stored at −80° C.

Figures 19A, 19B:
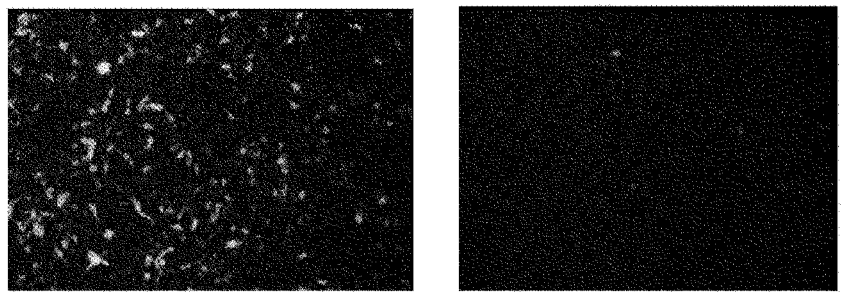
FIG. 19A is a diagram depicting infection of 293FT cell by HPV 16 L1 pseudotype virus.
FIG. 19B is a diagram depicting neutralization of HPV 16 L1 pseudotype virus by murine serum.

293FT cells were plated onto 24-well cell culture plate ($1.5 \times 10^5$ cells/well). Twenty-four hours later, neutralization experiment was done as follows. Different serum samples were serially diluted 100-fold with DMEM medium. An aliquot of 50 μL of each dilution was mixed with 50 μL of the pseudotype virus solution diluted in DMEM medium, and each mixture was incubated at 4° C. for 1 hour. Then each incubated mixture was added into the 24-well cell culture plate pre-plated with 293FT cells and incubated at 37° C. for 48 hours. After incubation, the cells were observed for expression of green fluorescent protein under an OLUMPUSCKX41F32FL inverted fluorescence microscope, and fluorescence images were collected, as shown in FIG. 19. Fluorescence was seen in FIG. 19A, which indicates that the HPV 16 pseudotype virus had infected the 293FT cells. Little fluorescence remained in FIG. 19B, which indicates that mouse serum had neutralized the HPV 16 pseudotype virus, thereby reducing the viral infection of the 293FT cells. It is therefore clear that mice immunized with recombinant HPV 16L1 VLPs vaccine could generate neutralizing antibody which would inhibit entry of the pseudotype virus into cells.

In the present invention, nucleotide sequence SEQ ID NO: 8 or SEQ ID NO: 9 can be substituted for SEQ ID NO: 7 in the above examples to prepare HPV 16 L1 protein of the present invention using the methods as described in the above examples. In addition, the above-said genes can also be cloned, in appropriate manner, into other existing *Pichia* yeast expression vector, such as pPIC6, pGAPZ or pAO815. Then the recombinant expression vectors obtained can be used to transform other *Pichia* yeast strains, such as *Pichia pastoris* GS115, KM71 or SMD1168 strains, so as to construct genetically engineered strains. Using conventional methods of culturing and fermentation, and separation and purification (which are not detailed herein), HPV 16 L1 protein (HPV 16 L1 VLPs) of the present invention can be obtained from the genetically engineered strains. The thus prepared HPV 16 L1 protein will have similar immunogenicity to that of the HPV 16 L1 protein prepared in the above examples.

All references cited in the present disclosure are hereby incorporated herein by reference as if each was individually incorporated herein by reference. In addition, it is understood that those skilled in the art will, in light of the teaching described hereinabove, make various changes and modifications to the present invention without departing from the spirit of the present invention, and these equivalents are deemed to fall within the scope of the present invention as defined in the appended claims.

What is claimed is:

1. An isolated gene encoding a major capsid protein L1 of human papilloma virus (HPV) or truncated version thereof, wherein said isolated gene is selected from the group consisting of: SEQ ID NO: 1, SEQ ID NO: 2, SEQ ID NO: 3, SEQ ID NO: 7, SEQ ID NO: 8, and SEQ ID NO: 9.

2. An expression vector, wherein said expression vector comprises the sequence of an isolated gene encoding the major capsid protein L1 of HPV or truncated version thereof, wherein said isolated gene is selected from the group consisting of: SEQ ID NO: 1, SEQ ID NO: 2, SEQ ID NO: 3, SEQ ID NO: 7, SEQ ID NO: 8, and SEQ ID NO: 9.

3. A genetically engineered isolated host cell, wherein said cell comprises the expression vector according to claim 2.

4. The isolated host cell according to claim 3, wherein said cell is *Pichia* yeast cell.

5. An immunogenic macromolecule, wherein said immunogenic macromolecule has a diameter of 50 to 80 nm and is self-assembled from the major capsid protein expressed by *Pichia* yeast transfected with the vector of claim 2.

6. A method for preparing the immunogenic macromolecule of claim 5, wherein said method comprises:
(1) culturing *Pichia* yeast transfected with the expression vector of claim 2 to allow said major capsid protein L1 of HPV to be expressed and to self-assemble into said immunogenic macromolecule and
(2) separating said immunogenic macromolecule from the yeast cell culture.

7. The method according to claim 6, wherein said step (2) further comprises:
(a) disrupting the yeast cells comprising the immunogenic macromolecules to obtain a supernatant comprising said immunogenic macromolecule; and
(b) purifying the supernatant obtained from step (a) using a first chromatographic column and a second chromatographic column to obtain said immunogenic macromolecule.

8. The method according to claim 7, wherein in said step (b), purification using the first chromatographic column is performed as follows:
(i) the supernatant obtain from step (a) is loaded onto a column having been cleaned and equilibrated to allow said immunogenic macromolecule to bind to the column;
(ii) the column is eluted with a linear gradient of 100% buffer A to 100% buffer B, and the chromatographic peaks at 70-100 ms/cm are collected,
wherein said buffer A contains 50.+−0.20 mM MOPS, 0.75.+−.0.3 M NaCl and 0.05.+−.0.02% polysorbate-80, at pH 6.5.+−0.1, and wherein said buffer B contains 50.+−0.20 mM MOPS, 1.5M NaCl and 0.05.+−.0.02% polysorbate-80, at pH 6.5.+−0.1;
and/or purification using the second chromatographic column is performed as follows:
(iii) the product purified from the first chromatographic column is loaded onto the second chromatographic column having been cleaned and equilibrated;
(iv) the second column is eluted with a linear gradient of 100% buffer C to 100% buffer D, and the chromatographic peaks 50-70 ms/cm are collected,
wherein said buffer C contains 50.+−0.20 mM MOPS, 0.5.+−.0.2 M NaCl, 0.04.+−.0.02 M phosphate buffer (PB) and 0.05.+−.0.02% polysorbate-80, at pH 6.5.+−0.1, and said buffer D contains 0.5.+−.0.2 M NaCl, 200 mM PB, and 0.05.+−.0.02% polysorbate-80, at pH 6.5.+−0.1.

9. An immunogenic composition, wherein said composition comprises:
(i) an effective amount of said immunogenic macromolecule according to claim 5; and
(ii) a pharmaceutically acceptable carrier.

10. A method for preventing or treating diseases related to HPV infection, wherein said method comprises administering to a subject in need thereof said immunogenic composition according to claim 9.

11. A genetically engineered isolated host cell, wherein said isolated cell has a gene integrated into its genome, wherein said gene encodes the major capsid protein L1 of claim 1.

12. The isolated host cell according to claim 11, wherein said cell is *Pichia* yeast cell.

13. A method for preparing the immunogenic macromolecule of claim 7, wherein said method comprises:
(1) culturing the *Pichia* yeast of claim 11 to allow said major capsid protein L1 of HPV to be expressed and to self-assemble into said immunogenic macromolecule and
(2) separating said immunogenic macromolecule from the yeast cell culture.

14. The method according to claim 13, wherein said step (2) further comprises:
(a) disrupting the yeast cells comprising the immunogenic macromolecules to obtain a supernatant comprising said immunogenic macromolecule; and
(b) purifying the supernatant obtained from step (a) using a first chromatographic column and a second chromatographic column to obtain said immunogenic macromolecule.

15. The method according to claim 14, wherein in said step (b), purification using the first chromatographic column is performed as follows:
- (i) the supernatant obtain from step (a) is loaded onto a column having been cleaned and equilibrated to allow said immunogenic macromolecule to bind to the column;
- (ii) the column is eluted with a linear gradient of 100% buffer A to 100% buffer B, and the chromatographic peaks at 70-100 ms/cm are collected, wherein said buffer A contains 50.+−0.20 mM MOPS, 0.75.+−.0.3 M NaCl and 0.05.+−.0.02% polysorbate-80, at pH 6.5.+−.1, and wherein said buffer B contains 50.+−0.20 mM MOPS, 1.5M NaCl and 0.05.+−.0.02% polysorbate-80, at pH 6.5.+−0.1; and/or purification using the second chromatographic column is performed as follows:

- (iii) the product purified from the first chromatographic column is loaded onto the second chromatographic column having been cleaned and equilibrated;
- (iv) the second column is eluted with a linear gradient of 100% buffer C to 100% buffer D, and the chromatographic peaks 50-70 ms/cm are collected, wherein said buffer C contains 50.+−0.20 mM MOPS, 0.5.+−.0.2 M NaCl, 0.04.+−.0.02 M phosphate buffer (PB) and 0.05.+−.0.02% polysorbate-80, at pH 6.5.+−0.1, and said buffer D contains 0.5.+−.0.2 M NaCl, 200 mM PB, and 0.05.+−.0.02% polysorbate-80, at pH 6.5.+−0.1.

* * * * *

UNITED STATES PATENT AND TRADEMARK OFFICE
CERTIFICATE OF CORRECTION

Page 1 of 2

PATENT NO. : 9,034,340 B2
APPLICATION NO. : 14/296700
DATED : May 19, 2015
INVENTOR(S) : Goaxia Zhang et al.

It is certified that error appears in the above-identified patent and that said Letters Patent is hereby corrected as shown below:

Specification

Column 3,
Line 25, "The supernatant obtain from ..." should be -- The supernatant obtained from --.

Column 6,
Lines 38-39, "...codons, such as, the codon for ..." should be -- ...codons, such as the codon for ... --.
Lines 45-46, "...thus obtaining a altered, novel HPV DNA sequences." should be -- ...thus obtaining altered, novel HPV DNA sequences. --.

Column 10,
Line 60, "This teen refers to ..." should be -- This term refers to ... --.

Column 22,
Line approx. 46, "...(g wet cells/L fermentation" should be -- ...(g wet cells/L fermentation broth). --.

Column 23,
Lines 1-2, "It can be seen from ... that, the optimized sequence of ..." should be -- It can be seen from ... that the optimized sequence of ... --.

Column 33,
Line 18, "It can be seen from ... that, the ..." should be -- It can be seen from ... that the ... --.
Lines 30-31, "...yeast cells expressing ... was thawed ..." should be -- ...yeast cells expressing ... were thawed ..." --.

Signed and Sealed this
Twenty-fourth Day of November, 2015

Michelle K. Lee
*Director of the United States Patent and Trademark Office*

CERTIFICATE OF CORRECTION (continued)
U.S. Pat. No. 9,034,340 B2

Specification

<u>Column 34,</u>
Lines 49-50, "The parameters of ... is as following:" should be -- The parameters of ... are as follows: --.

Claims

<u>Column 61,</u>
Line 59 (Claim 8), "...(i) the supernatant obtain from ..." should be -- ...(i) the supernatant obtained from ... --.
Lines 66-67 (Claim 8), "...wherein said buffer A contains 50.+-.0.20 mM MOPS, 0.75.+-.0.3 M NaCl and 0.05.+-.0.02% polysorbate-80, ..." should be -- wherein said buffer A contains 50 ± 20 mM MOPS, 0.75 ± 0.3 M NaCl and 0.05 ± 0.02% polysorbate-80, ... --.

<u>Column 62,</u>
Lines 1-3 (Claim 8), "...at pH 6.5.+-0.1, and wherein said buffer B contains 50.+-0.20 mM MOPS, 1.5M NaCl and 0.05.+-.0.02% polysorbate-80, at pH 6.5.+-0.1;" should be -- ...at pH 6.5 ± 1, and wherein said buffer B contains 50 ± 20 mM MOPS, 1.5 M NaCl and 0.05 ± 0.02% polysorbate-80, at pH 6.5 ± 1; --.
Lines 30-35 (Claim 8), "...wherein said buffer C contains 50.+-0.20 mM MOPS, 0.5.+-.0.2 M NaCl, 0.04.+-.0.02 M phosphate buffer (PB) and 0.05.+-.0.02% polysorbate-80, at pH 6.5.+- 0.1, and said buffer D contains 0.5.+-.0.2 M NaCl, 200 mM PB, and 0.05.+-.0.02% polysorbate-80, at pH 6.5.+-0.1." should be -- ...wherein said buffer C contains 50 ± 20 mM MOPS, 0.5 ± 0.2 M NaCl, 0.04 ± 0.02 M phosphate buffer (PB) and 0.05 ± 0.02% polysorbate-80, at pH 6.5 ± 1, and said buffer D contains 0.5 ± 0.2 M NaCl, 200 mM PB, and 0.05 ± 0.02% polysobate-80, at pH 6.5 ± 1. --.

<u>Column 63,</u>
Line 4 (Claim 15), "...(i) the supernatant obtain from ..." should be -- ...(i) the supernatant obtained from ... --.
Lines 11-15 (Claim 15), "...wherein said buffer A contains 50.+-0.20 mM MOPS, 0.75.+-.0.3 M NaCl and 0.05.+-.0.02% polysorbate-80, at pH 6.5.+-.1, and wherein said buffer B contains 50.+-0.20 mM MOPS, 1.5M NaCl and 0.05.+-.0.02% polysorbate-80, at pH 6.5.+-0.1; and/or purification ..." should be -- ...wherein said buffer A contains 50 ± 20 mM MOPS, 0.75 ± 0.3 M NaCl and 0.05 ± 0.02% polysorbate-80, at pH 6.5 ± 1, and wherein said buffer B contains 50 ± 20 mM MOPS, 1.5M NaCl and 0.05 ± 0.02% polysorbate-80, at pH 6.5 ± 1; and/or purification ... --.
Lines 24-29 (Claim 15), "...wherein said buffer C contains 50.+-0.20 mM MOPS, 0.5.+-.0.2 M NaCl, 0.04.+-.0.02 M phosphate buffer (PB) and 0.05.+-.0.02% polysorbate-80, at pH 6.5.+-0.1, and said buffer D contains 0.5.+-.0.2 M NaCl, 200 mM PB, and 0.05.+-.0.02% polysorbate-80, at pH 6.5.+-0.1." should be -- ... wherein said buffer C contains 50 ± 20 mM MOPS, 0.5 ± 0.2 M NaCl, 0.04 ± 0.02 M phosphate buffer (PB) and 0.05 ± 0.02% polysorbate-80, at pH 6.5 ± 1, and said buffer D contains 0.5 ± 0.2M NaCl, 200 mM PB, and 0.05 ± 0.02% polysorbate-80, at pH 6.5 ± 1. --.

SEQUENCE LISTING

<160> NUMBER OF SEQ ID NOS: 19

<210> SEQ ID NO 1
<211> LENGTH: 1524
<212> TYPE: DNA
<213> ORGANISM: Artificial Sequence
<220> FEATURE:

<223> OTHER INFORMATION: Synthesized

<400> SEQUENCE: 1

| | |
|---|---|
| atggctttgt ggagaccttc tgacaacact gtttacttgc cacctccatc cgttgctaga | 60 |
| gttgttaaca ctgatgacta cgttactaga acttctattt tctaccacgc tggttcctct | 120 |
| agattgttga ctgttggtaa cccttacttt agagttccag ctggtggtgg taacaagcaa | 180 |
| gatattccta aggtttccgc ttaccaatac agagttttca gagttcaatt gccagaccct | 240 |
| aacaagtttg gtttgccaga tacttctatt tacaaccctg agactcaaag attggtttgg | 300 |
| gcttgtgctg gtgttgaaat tggtagaggt caaccattgg gtgttggttt gtccggtcat | 360 |
| cctttctaca acaagttgga cgatactgag tcttcccacg ctgctacttc taacgtttcc | 420 |
| gaagacgtta gagataacgt ttctgttgac tacaagcaaa ctcaattgtg tattttgggt | 480 |
| tgtgctccag ctattggtga gcattgggct aagggtactg cttgtaagtc cagacctttg | 540 |
| tctcaaggtg attgtccacc tttgaattg aagaacactg ttttggagga cggtgatatg | 600 |
| gttgacactg ttacggtgc tatggatttc tccactttgc aagacactaa gtgtgaagtt | 660 |
| ccattggata tttgtcaatc tatttgtaag taccctgact acttgcaaat gtccgctgat | 720 |
| ccatacggtg actctatgtt cttttgtttg agaagagagc aattgttcgc tagacacttt | 780 |
| tggaacagag ctggtactat gggtgatact gttcctcaat ccttgtacat taagggtact | 840 |
| ggtatgagag cttctccagg ttcctgtgtt tactctcctt ccccatctgg ttccattgtt | 900 |
| acttctgact cccaattgtt caacaagcct tactggttgc ataaggctca aggtcacaac | 960 |
| aacggtgttt gttggcataa ccaattgttt gttactgttg ttgatactac tagatccact | 1020 |
| aacttgacta tttgtgcttc cactcaatct ccagttcctg gtcaatacga cgctactaag | 1080 |
| ttcaagcaat actccagaca cgttgaagag tacgatttgc aattcatctt ccaattgtgt | 1140 |
| actattactt tgactgctga cgttatgtct tacattcatt ccatgaactc ttccattttg | 1200 |
| gaagattgga ctttggtgt tccacctcca cctactactc ttggttga cacttacaga | 1260 |
| ttcgttcaat ccgttgctat tacttgtcaa aaggatgctg ctccagctga aacaaggac | 1320 |
| ccttacgata gttgaagtt ttggaacgtt gacttgaagg aaaagttctc tttggatttg | 1380 |
| gaccaatacc cattgggtag aaagttttg gttcaagctg gtttgagaag aaagcctact | 1440 |
| attggtccaa gaaagagatc cgctccttct gctactactt cctctaagcc agctaagaga | 1500 |
| gttagagtta gagctagaaa gtaa | 1524 |

<210> SEQ ID NO 2
<211> LENGTH: 1524
<212> TYPE: DNA
<213> ORGANISM: Artificial sequence
<220> FEATURE:
<223> OTHER INFORMATION: Synthesized

<400> SEQUENCE: 2

| | |
|---|---|
| atggctttgt ggagaccatc tgacaatact gtttacttgc caccaccatc tgttgctaga | 60 |
| gttgttaata ctgacgacta cgttactaga acttctattt tttaccatgc tggttcttct | 120 |
| agattgttga ctgttggtaa tccatacttt agagttccag ctggtggtgg taataaacaa | 180 |
| gacattccaa agtttctgc ttaccaatac agagttttta gagttcaatt gccagaccca | 240 |
| aataaatttg gtttgccaga cacttctatt tacaatccag aaactcaaag attggtttgg | 300 |
| gcttgtgctg gtgttgaaat tggtagaggt caaccattgg gtgttggttt gtctggtcat | 360 |
| ccatttaca ataaattgga cgacactgaa tcttctcatg ctgctacttc taatgtttct | 420 |

```
gaagacgtta gagacaatgt ttctgttgac tacaaacaaa ctcaattgtg tattttgggt      480
tgtgctccag ctattggtga acattgggct aaaggtactg cttgtaaatc tagaccattg      540
tctcaaggtg actgtccacc attggaattg aaaaatactg ttttggaaga cggtgacatg      600
gttgacactg ttacggtgc tatggacttt tctactttgc aagacactaa atgtgaagtt       660
ccattggaca tttgtcaatc tatttgtaaa tacccagact acttgcaaat gtctgctgac      720
ccatacggtg actctatgtt ttttgtttg agaagagaac aattgtttgc tagacatttt       780
tggaatagag ctggtactat gggtgacact gttccacaat cttttgtacat taaaggtact    840 ggtatgagag cttctccagg ttcttgtgtt tactctccat ctccatctgg ttctattgtt      900
acttctgact ctcaattgtt taataaacca tactggttgc ataaagctca aggtcataat     960
aatggtgttt gttggcataa tcaattgttt gttactgttg ttgacactac tagatctact     1020
aatttgacta tttgtgcttc tactcaatct ccagttccag gtcaatacga cgctactaaa     1080
tttaaacaat actctagaca tgttgaagaa tacgacttgc aatttatttt tcaattgtgt     1140
actattactt tgactgctga cgttatgtct tacattcatt ctatgaattc ttctatttg      1200 gaagactgga attttggtgt tccaccacca ccaactactt ctttggttga cacttacaga    1260
tttgttcaat ctgttgctat tacttgtcaa aaagacgctg ctccagctga aaataaagac   1320
ccatacgaca aattgaaatt ttggaatgtt gacttgaaag aaaaattttc tttggacttg    1380
gaccaatacc cattgggtag aaaattttg gttcaagctg gtttgagaag aaaaccaact    1440
attggtccaa gaaaaagatc tgctccatct gctactactt cttctaaacc agctaaaaga     1500
gttagagtta gagctagaaa ataa                                            1524
```

<210> SEQ ID NO 3
<211> LENGTH: 1524
<212> TYPE: DNA
<213> ORGANISM: Artificial sequence
<220> FEATURE:
<223> OTHER INFORMATION: Synthesized

<400> SEQUENCE: 3

```
atggctttgt ggagaccatc tgataacact gtttatttgc caccaccatc tgttgctaga       60
gttgttaaca ctgatgatta tgttactaga acttctatttt tctatcatgc tggatcttct    120
agattgttga ctgttggaaa cccatatttc agagttccag ctggaggagg aaacaagcaa     180
gatattccaa aggtttctgc ttatcaatat agagttttca gagttcaatt gccagatcca    240
aacaagttcg gattgccaga tacttctatt tataacccag aaactcaaag attggtttgg     300
gcttgtgctg gagttgaaat tggaagagga caaccattgg gagttggatt gtctggacat    360
ccattctata caagttgga tgatactgaa tcttctcatg ctgctacttc taacgttct       420 gaagatgtta gagataacgt ttctgttgat tataagcaaa ctcaattgtg tattttggga   480
tgtgctccag ctattggaga acattgggct aagggaactg cttgtaagtc tagaccattg     540
tctcaaggag attgtccacc attggaattg aagaacactg ttttggaaga tggagatatg    600
gttgatactg gatatggagc tatggatttc tctactttgc aagatactaa gtgtgaagtt    660
ccattggata tttgtcaatc tatttgtaag tatccagatt atttgcaaat gtctgctgat     720
ccatatggag attctatgtt cttctgtttg agaagagaac aattgttcgc tagacatttc   780
tggaacagag ctggaactat gggagatact gttccacaat cttttgtatat taagggaact    840 ggaatgagag cttctccagg atcttgtgtt tattctccat ctccatctgg atctattgtt    900
```

-continued

| | |
|---|---|
| acttctgatt ctcaattgtt caacaagcca tattggttgc ataaggctca aggacataac | 960 |
| aacggagttt gttggcataa ccaattgttc gttactgttg ttgatactac tagatctact | 1020 |
| aacttgacta tttgtgcttc tactcaatct ccagttccag acaatatga tgctactaag | 1080 |
| ttcaagcaat attctagaca tgttgaagaa tatgatttgc aattcatttt ccaattgtgt | 1140 |
| actattactt tgactgctga tgttatgtct tatattcatt ctatgaactc ttctattttg | 1200 |
| gaagattgga acttcggagt tccaccacca ccaactactt cttggttgac tacttataga | 1260 |
| ttcgttcaat ctgttgctat tacttgtcaa aaggatgctg ctccagctga aacaaggat | 1320 |
| ccatatgata agttgaagtt ctggaacgtt gatttgaagg aaaagttctc tttggatttg | 1380 |
| gatcaatatc cattgggaag aaagttcttg gttcaagctg gattgagaag aaagccaact | 1440 |
| attggaccaa gaaagagatc tgctccatct gctactactt cttctaagcc agctaagaga | 1500 |
| gttagagtta gagctagaaa gtaa | 1524 |

<210> SEQ ID NO 4
<211> LENGTH: 1707
<212> TYPE: DNA
<213> ORGANISM: Artificial sequence
<220> FEATURE:
<223> OTHER INFORMATION: Synthesized

<400> SEQUENCE: 4

| | |
|---|---|
| atgtgtttgt acactagagt tttgattttg cactaccatt tgttgccttt gtacggtcca | 60 |
| ttgtaccacc ctcaaccatt gcctttgcat tccattttgg tttacatggt tcacattatc | 120 |
| atttgtggtc attacattat tttgttcttg agaaacgtta acgttttccc aatcttcttg | 180 |
| caaatggctt tgtggagacc ttctgacaac actgtttact tgccacctcc atccgttgct | 240 |
| agagttgtta acactgatga ctacgttact agaacttcta ttttctacca cgctggttcc | 300 |
| tctagattgt tgactgttgg taacccttac tttagagttc agctggtgg tggtaacaag | 360 |
| caagatattc ctaaggtttc cgcttaccaa tacagagttc tcagagttca attgccagac | 420 |
| cctaacaagt ttggtttgcc agatacttct atttacaacc ctgagactca agattggtt | 480 |
| tgggcttgtg ctggtgttga aattggtaga ggtcaaccat tgggtgttgg tttgtccggt | 540 |
| catccttttct acaacaagtt ggacgatact gagtcttccc acgctgctac ttctaacgtt | 600 |
| tccgaagacg ttagagataa cgtttctgtt gactacaagc aaactcaatt gtgtattttg | 660 |
| ggttgtgctc cagctattgg tgagcattgg ctaagggta ctgcttgtaa gtccagacct | 720 |
| ttgtctcaag gtgattgtcc acctttggaa ttgaagaaca ctgttttgga ggacggtgat | 780 |
| atggttgaca ctggttacgg tgctatggat ttctccactt gcaagacac taagtgtgaa | 840 |
| gttccattgg atatttgtca atctatttgt aagtaccctg actacttgca aatgtccgct | 900 |
| gatccatacg gtgactctat gttctttgt ttgagaagag agcaattgtt cgctagacac | 960 |
| ttttggaaca gagctggtac tatgggtgat actgttcctc aatccttgta cattaagggt | 1020 |
| actggtatga gagcttctcc aggttcctgt gtttactctc cttccccatc tggttccatt | 1080 |
| gttacttctg actcccaatt gttcaacaag ccttactggt tgcataaggc tcaaggtcac | 1140 |
| aacaacggtg tttgttggca taaccaattg tttgttactg ttgatac tactagatcc | 1200 |
| actaacttga ctatttgtgc ttccactcaa tctccagttc ctggtcaata cgacgctact | 1260 |
| aagttcaagc aatactccag acacgttgaa gagtacgatt tgcaattcat cttccaattg | 1320 |
| tgtactatta ctttgactgc tgacgttatg tcttacattc attccatgaa ctcttccatt | 1380 |
| ttggaagatt ggaactttgg tgttccacct ccacctacta cttctttggt tgacacttac | 1440 |

```
agattcgttc aatccgttgc tattacttgt caaaaggatg ctgctccagc tgagaacaag    1500 gaccccttacg ataagttgaa gttttggaac gttgacttga aggaaaagtt ctctttggat    1560
ttggaccaat acccattggg tagaaagttt ttggttcaag ctggtttgag aagaaagcct    1620
actattggtc caagaaagag atccgctcct tctgctacta cttcctctaa gccagctaag    1680
agagttagag ttagagctag aaagtaa                                         1707
```

<210> SEQ ID NO 5
<211> LENGTH: 1707
<212> TYPE: DNA
<213> ORGANISM: Artificial sequence
<220> FEATURE:
<223> OTHER INFORMATION: Synthesized

<400> SEQUENCE: 5

```
atgtgtttgt acactagagt tttgattttg cattaccatt tgttgccatt gtacggtcca      60
ttgtaccatc cacaaccatt gccattgcat tctatttggg tttacatggt tcatattatt     120
atttgtggtc attacattat tttgtttttg agaaatgtta atgttttttcc aattttttttg   180 caaatggctt tgtggagacc atctgacaat actgttact tgccaccacc atctgttgct      240
agagttgtta atactgacga ctacgttact agaacttcta ttttttacca tgctggttct     300
tctagattgt tgactgttgg taatccatac tttagagttc cagctggtgg tggtaataaa     360
caagacattc caaaagtttc tgcttaccaa tacagagttt ttagagttca attgccagac     420
ccaaataaat ttggttttgcc agacacttct atttacaatc cagaaactca agattggtt    480 tgggcttgtg ctggtgttga aattggtaga ggtcaaccat gggtgttgg tttgtctggt      540 catccatttt acaataaatt ggacgacact gaatcttctc atgctgctac ttctaatgtt     600
tctgaagacg ttagagacaa tgtttctgtt gactacaaac aaactcaatt gtgtattttg     660
ggttgtgctc cagctattgg tgaacattgg gctaaaggta ctgcttgtaa atctagacca     720
ttgtctcaag gtgactgtcc accattggaa ttgaaaaata ctgttttgga agacggtgac     780
atggttgaca ctggttacgg tgctatggac ttttctactt tgcaagacac taaatgtgaa     840
gttccattgg acatttgtca atctatttgt aaatacccag actacttgca aatgtctgct     900
gacccatacg gtgactctat gttttttttgt ttgagaagag aacaattgtt gctagacat     960 ttttggaata gagctggtac tatgggtgac actgttccac aatctttgta cattaaaggt    1020
actggtatga gagcttctcc aggttcttgt gtttactctc catctccatc tggttctatt    1080
gttacttctg actctcaatt gtttaataaa ccatactggt tgcataaagc tcaaggtcat    1140
aataatggtg tttgttggca taatcaattg tttgttactg ttgttgacac tactagatct    1200
actaatttga ctatttgtgc ttctactcaa tctccagttc caggtcaata cgacgctact    1260
aaatttaaac aatactctag acatgttgaa gaatacgact gcaatttat ttttcaattg     1320 tgtactatta ctttgactgc tgacgttatg tcttacattc attctatgaa ttcttctatt    1380
ttggaagact ggaattttgg tgttccacca ccaccaacta cttctttggt tgacacttac    1440
agatttgttc aatctgttgc tattacttgt caaaagacg ctgctccagc tgaaaataaa     1500
gacccatacg acaaattgaa attttggaat gttgacttga agaaaaatt ttctttggac    1560 ttggaccaat acccattggg tagaaaattt ttggttcaag ctggtttgag aagaaaacca    1620
actattggtc caagaaaaag atctgctcca tctgctacta cttcttctaa accagctaaa    1680
agagttagag ttagagctag aaaataa                                          1707
```

<210> SEQ ID NO 6
<211> LENGTH: 1707
<212> TYPE: DNA
<213> ORGANISM: Artificial sequence
<220> FEATURE:
<223> OTHER INFORMATION: Synthesized

<400> SEQUENCE: 6

```
atgtgtttgt atactagagt tttgattttg cattatcatt tgttgccatt gtatggacca      60
ttgtatcatc cacaaccatt gccattgcat tctattttgg tttatatggt tcatattatt     120
atttgtggac attatattat tttgttcttg agaaacgtta acgttttccc aattttcttg     180
caaatggctt tgtggagacc atctgataac actgtttatt gccaccacc atctgttgct      240
agagttgtta acactgatga ttatgttact agaacttcta ttttctatca tgctggatct     300
tctagattgt tgactgttgg aaacccatat ttcagagttc agctggagg aggaaacaag      360
caagatattc caaggtttc tgcttatcaa tatagagttt tcagagttca attgccagat      420
ccaaacaagt tcggattgcc agatacttct atttataacc cagaaactca aagattggtt     480
tgggcttgtg ctggagttga aattggaaga ggacaaccat gggagttgg attgtctgga      540
catccattct ataacaagtt ggatgatact gaatcttctc atgctgctac ttctaacgtt     600
tctgaagatg ttagagataa cgtttctgtt gattataagc aaactcaatt gtgtattttg     660
ggatgtgctc cagctattgg agaacattgg gctaagggaa ctgcttgtaa gtctagacca     720
ttgtctcaag agattgtcc accattggaa ttgaagaaca ctgttttgga agatggagat      780
atggttgata ctggatatgg agctatggat ttctctactt tgcaagatac taagtgtgaa     840
gttccattgg atatttgtca atctatttgt aagtatccag attatttgca aatgtctgct     900
gatccatatg gagattctat gttcttctgt ttgagaagag aacaattgtt cgctagacat     960
ttctggaaca gagctggaac tatgggagat actgttccac aatctttgta tattaaggga    1020
actgaatgga gcttctcc aggatcttgt gtttattctc catctccatc tggatctatt      1080
gttacttctg attctcaatt gttcaacaag ccatattggt tgcataaggc tcaaggacat    1140
aacaacggag tttgttggca taaccaattg ttcgttactg ttgttgatac tactagatct    1200
actaacttga ctatttgtgc ttctactcaa tctccagttc aggacaata tgatgctact     1260
aagttcaagc aatattctag acatgttgaa gaatatgatt tgcaattcat tttccaattg    1320
tgtactatta ctttgactgc tgatgttatg tcttatattc attctatgaa ctcttctatt    1380
ttggaagatt ggaacttcgg agttccacca ccaccaacta cttctttggt tgatacttat    1440
agattcgttc aatctgttgc tattacttgt caaaaggatg ctgctccagc tgaaaacaag    1500
gatccatatg ataagttgaa gttctggaac gttgatttga aggaaaagtt ctcttttggat    1560
ttggatcaat atccattggg aagaaagttc ttggttcaag ctggattgag aagaaagcca    1620
actattggac aagaaagag atctgctcca tctgctacta cttcttctaa gccagctaag    1680
agagttagag ttagagctag aaagtaa                                        1707
```

<210> SEQ ID NO 7
<211> LENGTH: 1518
<212> TYPE: DNA
<213> ORGANISM: Artificial sequence
<220> FEATURE:
<223> OTHER INFORMATION: Synthesized

<400> SEQUENCE: 7

```
atgtctttgt ggttgccatc tgaagctact gtttacttgc caccagttcc agtttctaag      60
```

```
gttgtttcta ctgatgaata cgttgctaga actaacattt actaccatgc tggtacttct      120
agattgttgg ctgttggtca cccatacttt ccaattaaga agccaaacaa caacaagatt      180
ttggttccaa aggtttctgg tttgcaatac agagttttta gaatccattt gccagatcca      240
aacaagtttg gttttccaga tacttctttt tacaacccag atactcaaag attggtttgg      300
gcttgtgttg gtgttgaagt tggtagaggt caaccattgg gtgttggtat ttctggtcac      360
ccattgttga caagttggga tgatactgaa acgcttctg cttacgctgc taacgctggt       420
gttgataaca gagaatgtat ttctatggat tacaagcaaa ctcaattgtg tttgattggt      480
tgtaagccac caattggtga acattggggt aagggttctc catgtactaa cgttgctgtt      540
aacccaggtg attgtccacc attggaattg attaacactg ttattcaaga tggtgatatg      600
gttgatactg gttttggtgc tatggatttt actactttgc aagctaacaa gtctgaagtt      660
ccattggata tttgtacttc tatttgtaag tacccagatt acattaagat ggtttctgaa      720
ccatacggta ttctttgtt ttttacttg agaagagaac aaatgtttgt tagacacttg        780
tttaacagag ctggtgctgt tggtgaaaac gttccagatg atttgtacat taagggttct      840
ggttctactg ctaacttggc ttcttctaac tactttccaa ctccatctgg ttctatggtt      900
acttctgatg ctcaaatttt taacaagcca tactggttgc aaagagccca aggtcataac      960
aacggtattt gttggggtaa ccaattgttt gttactgttg ttgatactac tagatctact     1020
aacatgtctt tgtgtgctgc tatttctact tctgaaacta cttacaagaa cactaacttt     1080
aaggaatact tgagacacgg tgaagaatac gatttgcaat ttattttca attgtgtaag      1140 attactttga ctgctgatgt tatgacttac attcattcta tgaactctac tattttggaa     1200
gattggaact ttggtttgca accaccacca ggtggtactt ggaagatac ttacagattt       1260 gttacttctc aagctattgc ttgtcaaaag cacactccac cagctccaaa ggaagatcca     1320
ttgaagaagt acactttttg ggaagttaac ttgaaggaaa agttttctgc tgatttggat     1380
caatttccat tgggtagaaa gtttttgttg caagctggtt gaaggctaa gccaaagttt      1440 actttgggta agagaaaggc tactccaact acttcttcta cttctactac tgctaagaga     1500
aagaagagaa agttgtaa                                                    1518
```

<210> SEQ ID NO 8
<211> LENGTH: 1521
<212> TYPE: DNA
<213> ORGANISM: Artificial sequence
<220> FEATURE:
<223> OTHER INFORMATION: Synthesized

<400> SEQUENCE: 8

```
atgtctttgt ggttgccatc tgaagctact gtttacttgc caccagttcc agtttctaaa       60
gttgtttcta ctgacgaata cgttgctaga actaatattt actaccatgc tggtacttct      120
agattgttgg ctgttggtca tccatacttt ccaattaaaa aaccaaataa taataaaatt      180
ttggttccaa aagtttctgg tttgcaatac agagttttta gaattcattt gccagaccca      240
aataaatttg gttttccaga cacttctttt tacaatccag acactcaaag attggtttgg      300
gcttgtgttg gtgttgaagt tggtagaggt caaccattgg gtgttggtat ttctggtcat      360
ccattgttga ataaattgga cgacactgaa aatgcttctg cttacgctgc taatgctggt      420
gttgacaata gagaatgtat ttctatggac tacaaacaaa ctcaattgtg tttgattggt      480
tgtaaaccac caattggtga acattggggt aaaggttctc catgtactaa tgttgctgtt      540
```

```
aatccaggtg actgtccacc attggaattg attaatactg ttattcaaga cggtgacatg    600
gttgacactg gttttggtgc tatggacttt actactttgc aagctaataa atctgaagtt    660
ccattggaca tttgtacttc tatttgtaaa tacccagact acattaaaat ggtttctgaa    720
ccatacggtg actctttgtt tttttacttg agaagagaac aaatgtttgt tagacatttg    780
tttaatagag ctggtgctgt tggtgaaaat gttccagacg acttgtacat taaaggttct    840
ggttctactg ctaatttggc ttcttctaat tactttccaa ctccatctgg ttctatggtt    900
acttctgacg ctcaaatttt taataaacca tactggttgc aaagagctca aggtcataat    960
aatggtattt gttggggtaa tcaattgttt gttactgttg ttgacactac tagatctact   1020
aatatgtctt tgtgtgctgc tatttctact tctgaaacta cttacaaaaa tactaatttt   1080
aaagaatact tgagacatgg tgaagaatac gacttgcaat ttattttca attgtgtaaa    1140 attactttga ctgctgacgt tatgacttac attcattcta tgaattctac tattttggaa   1200
gactggaatt ttggtttgca accaccacca ggtggtactt tggaagacac ttacagattt   1260
gttacttctc aagctattgc ttgtcaaaaa catactccac cagctccaaa agaagaccca   1320
ttgaaaaaat acacttttg ggaagttaat ttgaaagaaa aattttctgc tgacttggac    1380
caatttccat gggtagaaa atttttgttg caagctggtt tgaaagctaa accaaaattt    1440
actttgggta aagaaaagc tactccaact acttcttcta cttctactac tgctaaaaga   1500 aaaaaagaa aattgtaata g                                              1521

<210> SEQ ID NO 9
<211> LENGTH: 1521
<212> TYPE: DNA
<213> ORGANISM: Artificial sequence
<220> FEATURE:
<223> OTHER INFORMATION: Synthesized

<400> SEQUENCE: 9
atgtctttgt ggttgccatc tgaagctact gtttatttgc caccagttcc agtttctaag     60
gttgtttcta ctgatgaata tgttgctaga actaacattt attatcatgc tggaacttct    120
agattgttgg ctgttggaca tccatatttc ccaattaaga agccaaacaa caacaagatt    180
ttggttccaa aggtttctgg attgcaatat agagttttca gaattcattt gccagatcca    240
aacaagttcg gattcccaga tacttctttc tataacccag atactcaaag attggtttgg    300
gcttgtgttg gagttgaagt tggaagagga caaccattgg gagttggaat ttctggacat    360
ccattgttga caagttgga tgatactgaa aacgcttctg cttatgctgc taacgctgga    420
gttgataaca gagaatgtat ttctatggat tataagcaaa ctcaattgtg tttgattgga    480
tgtaagccac caattggaga acattgggga aagggatctc catgtactaa cgttgctgtt    540
aacccaggag attgtccacc attggaattg attaacactg ttattcaaga tggagatatg    600
gttgatactg gattcggagc tatggatttc actactttgc aagctaacaa gtctgaagtt    660
ccattggata tttgtacttc tatttgtaag tatccagatt atattaagat ggtttctgaa    720
ccatatggag attctttgtt cttctatttg agaagagaac aaatgttcgt tagacatttg    780
ttcaacagag ctggagctgt tggagaaaac gttccagatg atttgtatat taagggatct    840
ggatctactg ctaacttggc ttcttctaac tatttcccaa ctccatctgg atctatggtt    900
acttctgatg ctcaaatttt caacaagcca tattggttgc aaagagctca aggacataac    960
aacggaattt gttggggaaa ccaattgttc gttactgttg ttgatactac tagatctact   1020
aacatgtctt tgtgtgctgc tatttctact tctgaaacta cttataagaa cactaacttc   1080
```

```
aaggaatatt tgagacatgg agaagaatat gatttgcaat tcattttcca attgtgtaag   1140
attactttga ctgctgatgt tatgacttat attcattcta tgaactctac tattttggaa   1200
gattggaact tcggattgca accaccacca ggaggaactt tggaagatac ttatagattc   1260
gttacttctc aagctattgc ttgtcaaaag catactccac cagctccaaa ggaagatcca   1320
ttgaagaagt atactttctg ggaagttaac ttgaaggaaa agttctctgc tgatttggat   1380
caattcccat tgggaagaaa gttcttgttg caagctggat tgaaggctaa gccaaagttc   1440
actttgggaa agagaaaggc tactccaact acttcttcta cttctactac tgctaagaga   1500
aagaagagaa agttgtaata g                                             1521

<210> SEQ ID NO 10
<211> LENGTH: 568
<212> TYPE: PRT
<213> ORGANISM: Alphapapillomavirus Human papillomavirus 18

<400> SEQUENCE: 10

Met Cys Leu Tyr Thr Arg Val Leu Ile Leu His Tyr His Leu Leu Pro
1               5                   10                  15

Leu Tyr Gly Pro Leu Tyr His Pro Gln Pro Leu Pro Leu His Ser Ile
            20                  25                  30

Leu Val Tyr Met Val His Ile Ile Cys Gly His Tyr Ile Ile Leu
        35                  40                  45

Phe Leu Arg Asn Val Asn Val Phe Pro Ile Phe Leu Gln Met Ala Leu
    50                  55                  60

Trp Arg Pro Ser Asp Asn Thr Val Tyr Leu Pro Pro Ser Val Ala
65                  70                  75                  80

Arg Val Val Asn Thr Asp Asp Tyr Val Thr Arg Thr Ser Ile Phe Tyr
                85                  90                  95

His Ala Gly Ser Ser Arg Leu Leu Thr Val Gly Asn Pro Tyr Phe Arg
            100                 105                 110

Val Pro Ala Gly Gly Asn Lys Gln Asp Ile Pro Lys Val Ser Ala
        115                 120                 125

Tyr Gln Tyr Arg Val Phe Arg Val Gln Leu Pro Asp Pro Asn Lys Phe
    130                 135                 140

Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                165                 170                 175

Gly Leu Ser Gly His Pro Phe Tyr Asn Lys Leu Asp Asp Thr Glu Ser
            180                 185                 190

Ser His Ala Ala Thr Ser Asn Val Ser Glu Asp Val Arg Asp Asn Val
        195                 200                 205

Ser Val Asp Tyr Lys Gln Thr Gln Leu Cys Ile Leu Gly Cys Ala Pro
    210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
            260                 265                 270

Thr Leu Gln Asp Thr Lys Cys Glu Val Pro Leu Asp Ile Cys Gln Ser
        275                 280                 285
```

```
Ile Cys Lys Tyr Pro Asp Tyr Leu Gln Met Ser Ala Asp Pro Tyr Gly
    290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Arg Ala Ser Pro Gly Ser Cys Val Tyr
            340                 345                 350

Ser Pro Ser Pro Ser Gly Ser Ile Val Thr Ser Asp Ser Gln Leu Phe
        355                 360                 365

Asn Lys Pro Tyr Trp Leu His Lys Ala Gln Gly His Asn Asn Gly Val
    370                 375                 380

Cys Trp His Asn Gln Leu Phe Val Thr Val Val Asp Thr Thr Arg Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
            420                 425                 430

Asp Leu Gln Phe Ile Phe Gln Leu Cys Thr Ile Thr Leu Thr Ala Asp
        435                 440                 445

Val Met Ser Tyr Ile His Ser Met Asn Ser Ser Ile Leu Glu Asp Trp
    450                 455                 460

Asn Phe Gly Val Pro Pro Pro Thr Thr Ser Leu Val Asp Thr Tyr
465                 470                 475                 480

Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
            500                 505                 510

Leu Lys Glu Lys Phe Ser Leu Asp Leu Asp Gln Tyr Pro Leu Gly Arg
        515                 520                 525

Lys Phe Leu Val Gln Ala Gly Leu Arg Arg Lys Pro Thr Ile Gly Pro
    530                 535                 540

Arg Lys Arg Ser Ala Pro Ser Ala Thr Thr Ser Ser Lys Pro Ala Lys
545                 550                 555                 560

Arg Val Arg Val Arg Ala Arg Lys
                565

<210> SEQ ID NO 11
<211> LENGTH: 505
<212> TYPE: PRT
<213> ORGANISM: Alphapapillomavirus Human papillomavirus 16

<400> SEQUENCE: 11

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95
```

```
Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505
```

```
<210> SEQ ID NO 12
<211> LENGTH: 29
<212> TYPE: DNA
<213> ORGANISM: Artificial Sequence
<220> FEATURE:
<223> OTHER INFORMATION: Synthesized

<400> SEQUENCE: 12
atagaattca tgtgtttgta cactagagt                                29

<210> SEQ ID NO 13
<211> LENGTH: 31
<212> TYPE: DNA
<213> ORGANISM: Artificial Sequence
<220> FEATURE:
<223> OTHER INFORMATION: Synthesized

<400> SEQUENCE: 13
aatggtaccc tattactttc tagctctaac t                             31

<210> SEQ ID NO 14
<211> LENGTH: 39
<212> TYPE: DNA
<213> ORGANISM: Artificial Sequence
<220> FEATURE:
<223> OTHER INFORMATION: Synthesized

<400> SEQUENCE: 14
tcccaatctt cgaaacgatg tgtttgtaca ctagagttt                     39

<210> SEQ ID NO 15
<211> LENGTH: 30
<212> TYPE: DNA
<213> ORGANISM: Artificial Sequence
<220> FEATURE:
<223> OTHER INFORMATION: Synthesized

<400> SEQUENCE: 15
tcccaatctt cgaaacgatg gctttgtgga                               30

<210> SEQ ID NO 16
<211> LENGTH: 29
<212> TYPE: DNA
<213> ORGANISM: Artificial Sequence
<220> FEATURE:
<223> OTHER INFORMATION: Synthesized

<400> SEQUENCE: 16
atagaattca tgtctttgtg gttgccatc                                29

<210> SEQ ID NO 17
<211> LENGTH: 31
<212> TYPE: DNA
<213> ORGANISM: Artificial Sequence
<220> FEATURE:
<223> OTHER INFORMATION: Synthesized

<400> SEQUENCE: 17
ataggtaccc tattacaact ttctcttctt t                             31

<210> SEQ ID NO 18
<211> LENGTH: 29
<212> TYPE: DNA
<213> ORGANISM: Artificial Sequence
<220> FEATURE:
<223> OTHER INFORMATION: Synthesized
```

```
<400> SEQUENCE: 18
actaattatt cgaaacgatg tctttgtgg                                                29

<210> SEQ ID NO 19
<211> LENGTH: 32
<212> TYPE: DNA
<213> ORGANISM: Artificial Sequence
<220> FEATURE:
<223> OTHER INFORMATION: Synthesized

<400> SEQUENCE: 19
agcggtaccc tattacaact ttctcttctt tc                                            32
```